(12) United States Patent  (10) Patent No.: US 7,935,063 B2
Roe  (45) Date of Patent: May 3, 2011

(54) SYSTEM AND METHOD FOR BREAKING A STERILITY SEAL TO ENGAGE A LANCET

(75) Inventor: Steven N. Roe, San Mateo, CA (US)

(73) Assignee: Roche Diagnostics Operations, Inc., Indianapolis, MN (US)

( * ) Notice: Subject to any disclaimer, the term of this patent is extended or adjusted under 35 U.S.C. 154(b) by 100 days.

(21) Appl. No.: 11/551,414

(22) Filed: Oct. 20, 2006

(65) Prior Publication Data

US 2007/0167869 A1    Jul. 19, 2007

Related U.S. Application Data

(63) Continuation-in-part of application No. 11/070,502, filed on Mar. 2, 2005, now Pat. No. 7,815,579, and a continuation-in-part of application No. 11/549,302, filed on Oct. 13, 2006.

(51) Int. Cl.
    *A61B 5/00*    (2006.01)
(52) U.S. Cl. ....................................................... 600/584
(58) Field of Classification Search .................. 600/584, 600/585, 583, 573, 345; 606/181, 182
    See application file for complete search history.

(56) References Cited

U.S. PATENT DOCUMENTS

| | | |
|---|---|---|
| 2,896,628 A | 7/1959 | Speelman |
| 3,640,267 A | 2/1972 | Hurtig et al. |
| 3,640,388 A | 2/1972 | Ferrari |
| 3,640,393 A | 2/1972 | Hurtig |
| 3,799,742 A | 3/1974 | Coleman |
| 4,360,016 A | 11/1982 | Sarrine |
| 4,627,445 A | 12/1986 | Garcia et al. |
| 4,637,403 A | 1/1987 | Garcia et al. |
| 4,787,398 A | 11/1988 | Garcia et al. |
| 4,790,979 A | 12/1988 | Terminiello et al. |
| 4,837,049 A | 6/1989 | Byers et al. |

(Continued)

FOREIGN PATENT DOCUMENTS

DE    2803345 B1    6/1979

(Continued)

OTHER PUBLICATIONS

U.S. Appl. No. 11/326,422, filed Jul. 1, 2004, Roe.

(Continued)

*Primary Examiner* — Max Hindenburg
*Assistant Examiner* — Fangemonique Smith
(74) *Attorney, Agent, or Firm* — Woodard, Emhardt, Moriarty, McNett & Henry LLP

(57) ABSTRACT

An integrated lancing test strip includes a test strip and a lancet packet coupled to the test strip. The lancet packet includes a sterility sheet enclosing a lancet to maintain the sterility of the lancet and prevent cross-contamination between the test strip and the lancet. The sterility sheet allows the lancet to be sterilized separately from the test strip. In one form, a firing mechanism has a blade that punctures and slits the sterility sheet during the firing cycle to reduce the chance of cross contamination between the lancet and the test strip prior to use. This allows an operator to load and subsequently remove an unused integrated lancing test strip without compromising the sterility of the lancet. The lancet includes an engagement opening in which the blade of the firing mechanism engages the lancet. The engagement opening is configured to reduce the chance of the blade becoming dull.

42 Claims, 13 Drawing Sheets

U.S. PATENT DOCUMENTS

| | | | |
|---|---|---|---|
| 4,873,993 | A | 10/1989 | Meserol et al. |
| 4,920,977 | A | 5/1990 | Haynes |
| 4,924,879 | A | 5/1990 | O'Brien |
| 4,995,402 | A | 2/1991 | Smith et al. |
| 5,014,718 | A | 5/1991 | Mitchen |
| 5,029,583 | A | 7/1991 | Meserol et al. |
| 5,035,704 | A | 7/1991 | Lambert et al. |
| 5,054,499 | A | 10/1991 | Swierczek |
| 5,217,480 | A | 6/1993 | Haber et al. |
| 5,231,993 | A | 8/1993 | Haber et al. |
| 5,290,420 | A | 3/1994 | Matson |
| 5,420,016 | A | 5/1995 | Boguslaski et al. |
| 5,514,152 | A | 5/1996 | Smith |
| 5,571,132 | A | 11/1996 | Mawhirt et al. |
| 5,591,139 | A | 1/1997 | Lin et al. |
| 5,636,640 | A | 6/1997 | Staehlin |
| 5,682,233 | A | 10/1997 | Brinda |
| 5,700,695 | A | 12/1997 | Yassinzadeh et al. |
| RE35,803 | E | 5/1998 | Lange et al. |
| 5,779,677 | A | 7/1998 | Frezza |
| 5,801,057 | A | 9/1998 | Smart et al. |
| 5,871,494 | A | 2/1999 | Simons et al. |
| 5,928,207 | A | 7/1999 | Pisano et al. |
| 5,938,679 | A | 8/1999 | Freeman et al. |
| 5,951,492 | A | 9/1999 | Douglas et al. |
| 5,971,941 | A | 10/1999 | Simons et al. |
| 6,036,924 | A | 3/2000 | Simons et al. |
| 6,048,352 | A | 4/2000 | Douglas et al. |
| 6,051,392 | A | 4/2000 | Ikdeda et al. |
| 6,071,294 | A | 6/2000 | Simons et al. |
| 6,120,676 | A | 9/2000 | Heller et al. |
| 6,235,539 | B1 | 5/2001 | Carpenter |
| 6,299,757 | B1 | 10/2001 | Feldman et al. |
| 6,315,738 | B1 | 11/2001 | Nishikawa et al. |
| 6,358,265 | B1 | 3/2002 | Thorne, Jr. et al. |
| 6,419,661 | B1 | 7/2002 | Kuhr et al. |
| 6,537,257 | B1 | 3/2003 | Wien |
| 6,561,989 | B2 | 5/2003 | Whitson |
| 6,612,111 | B1 | 9/2003 | Hodges et al. |
| 6,616,616 | B2 | 9/2003 | Fritz et al. |
| 6,620,112 | B2 | 9/2003 | Klitmose |
| 6,783,502 | B2 | 8/2004 | Orloff et al. |
| 6,866,675 | B2 | 3/2005 | Perez et al. |
| 6,939,312 | B2 | 9/2005 | Hodges et al. |
| 7,297,122 | B2 | 11/2007 | Boecker et al. |
| 7,299,081 | B2 | 11/2007 | Mace et al. |
| 2002/0052618 | A1 | 5/2002 | Haar et al. |
| 2002/0130042 | A1 | 9/2002 | Moerman et al. |
| 2002/0137998 | A1 | 9/2002 | Smart et al. |
| 2002/0168290 | A1 | 11/2002 | Yuzhakov et al. |
| 2002/0177763 | A1 | 11/2002 | Burns et al. |
| 2003/0018282 | A1 | 1/2003 | Effenhauser et al. |
| 2003/0024811 | A1 | 2/2003 | Davies et al. |
| 2003/0028087 | A1 | 2/2003 | Yuzhakov et al. |
| 2003/0028125 | A1 | 2/2003 | Yuzhakov et al. |
| 2003/0050573 | A1 | 3/2003 | Kuhr et al. |
| 2003/0083685 | A1 | 5/2003 | Freeman et al. |
| 2003/0083686 | A1 | 5/2003 | Freeman et al. |
| 2003/0143113 | A2 | 7/2003 | Yuzhakov et al. |
| 2003/0144608 | A1 | 7/2003 | Kojima et al. |
| 2003/0153939 | A1 | 8/2003 | Fritz et al. |
| 2003/0171699 | A1 | 9/2003 | Brenneman |
| 2003/0211619 | A1 | 11/2003 | Olson et al. |
| 2003/0212344 | A1 | 11/2003 | Yuzhakov et al. |
| 2003/0212345 | A1 | 11/2003 | McAllister et al. |
| 2003/0212346 | A1 | 11/2003 | Yuzhakov et al. |
| 2003/0212347 | A1 | 11/2003 | Sohrab |
| 2003/0223906 | A1 | 12/2003 | McAllister et al. |
| 2004/0034318 | A1 | 2/2004 | Fritz et al. |
| 2004/0064068 | A1 | 4/2004 | DeNuzzio et al. |
| 2004/0092842 | A1* | 5/2004 | Boecker et al. ............... 600/575 |
| 2004/0096959 | A1 | 5/2004 | Stiene et al. |
| 2004/0102717 | A1 | 5/2004 | Qi |
| 2004/0106941 | A1 | 6/2004 | Roe et al. |
| 2004/0120848 | A1 | 6/2004 | Teodorczyk |
| 2004/0127818 | A1 | 7/2004 | Roe |
| 2004/0127819 | A1 | 7/2004 | Roe et al. |
| 2004/0163987 | A1 | 8/2004 | Allen |
| 2004/0186394 | A1 | 9/2004 | Roe et al. |
| 2004/0193072 | A1 | 9/2004 | Allen |
| 2004/0193202 | A1 | 9/2004 | Allen |
| 2004/0206636 | A1 | 10/2004 | Hodges et al. |
| 2004/0225312 | A1 | 11/2004 | Orloff et al. |
| 2004/0236251 | A1 | 11/2004 | Roe et al. |
| 2005/0033341 | A1 | 2/2005 | Vreeke et al. |
| 2005/0049522 | A1 | 3/2005 | Allen |
| 2005/0139489 | A1 | 6/2005 | Davies et al. |
| 2005/0232815 | A1 | 10/2005 | Ruhl et al. |
| 2005/0234368 | A1 | 10/2005 | Wong et al. |
| 2005/0245844 | A1* | 11/2005 | Mace et al. .................. 600/583 |
| 2005/0245845 | A1 | 11/2005 | Roe et al. |
| 2005/0245954 | A1 | 11/2005 | Roe et al. |
| 2005/0251064 | A1 | 11/2005 | Roe |
| 2005/0277850 | A1 | 12/2005 | Mace et al. |
| 2005/0277881 | A1 | 12/2005 | Sibbitt |
| 2005/0283094 | A1 | 12/2005 | Thym et al. |
| 2006/0079810 | A1 | 4/2006 | Patel et al. |
| 2006/0100542 | A9 | 5/2006 | Wong et al. |
| 2006/0100543 | A1 | 5/2006 | Raney et al. |
| 2006/0106411 | A1 | 5/2006 | Schraga et al. |
| 2006/0174592 | A1 | 8/2006 | Chan |
| 2006/0216817 | A1 | 9/2006 | Hoenes et al. |
| 2006/0229532 | A1 | 10/2006 | Wong et al. |

FOREIGN PATENT DOCUMENTS

| | | |
|---|---|---|
| DE | 3515420 | 10/1986 |
| DE | 19855465 | 6/1999 |
| EP | 0127958 A2 | 5/1984 |
| EP | 0199484 B1 | 10/1986 |
| EP | 1374770 A1 | 1/2004 |
| EP | 1402812 A1 | 3/2004 |
| EP | 1 508 304 | 10/2006 |
| FR | 2590673 | 5/1987 |
| JP | 02-120655 A1 | 5/1990 |
| JP | 04-194660 A1 | 7/1992 |
| JP | 09-168530 A1 | 10/1995 |
| JP | 09-084781 A1 | 3/1997 |
| JP | 09-089885 A1 | 4/1997 |
| JP | 09-285459 | 11/1997 |
| JP | 09-294737 A1 | 11/1997 |
| JP | 09-313465 A1 | 12/1997 |
| JP | 10-005198 A1 | 1/1998 |
| JP | 10-005199 A1 | 1/1998 |
| JP | 10-005200 A1 | 1/1998 |
| JP | 10-014906 A1 | 1/1998 |
| JP | 10-024028 A1 | 1/1998 |
| JP | 10-033507 A1 | 2/1998 |
| JP | 10-033508 A1 | 2/1998 |
| JP | 2004-267760 A | 9/2004 |
| JP | 2006-518629 A | 8/2006 |
| WO | WO85/04089 A1 | 9/1985 |
| WO | WO86/00513 | 1/1986 |
| WO | WO91/06855 A1 | 5/1991 |
| WO | WO 98/14125 | 4/1998 |
| WO | WO2004/064636 A1 | 8/2004 |
| WO | WO2004/066822 A2 | 8/2004 |
| WO | WO 2004/075760 A1 | 9/2004 |
| WO | WO2005/104948 A1 | 11/2005 |
| WO | WO2005/104949 A1 | 11/2005 |
| WO | WO 2006/092281 A2 | 9/2006 |

OTHER PUBLICATIONS

U.S. Appl. No. 11/537,791, filed Oct. 2, 2006, Calasso et al.
International Patent Application PCT/EP2007/009069 International Search Report mailed Mar. 23, 2008.
PCT/EP2007/009069 International Preliminary Report on Patentability mailed Oct. 16, 2008.
Non-final Office Action mailed Dec. 30, 2009, in related U.S. Appl. No. 11/549,302, filed Oct. 13, 2006 to Roe et al.

* cited by examiner

SYSTEM AND METHOD FOR BREAKING A STERILITY SEAL TO ENGAGE A LANCET

REFERENCE TO RELATED APPLICATIONS

This application is a continuation-in-part of U.S. patent application Ser. No. 11/070,502, filed Mar. 2, 2005, entitled "DYNAMIC INTEGRATED LANCING TEST STRIP WITH STERILITY COVER" which is hereby incorporated by reference. This application is a continuation-in-part of U.S. patent application Ser. No. 11/549,302, filed Oct. 13, 2006 entitled "TAPE TRANSPORT LANCE SAMPLER", which is hereby incorporated by reference.

BACKGROUND

The present invention generally relates to bodily fluid sampling devices and more specifically, but not exclusively, concerns an integrated lancing test strip with a lancet contained within a sterility sheet.

The acquisition and testing of bodily fluids is useful for many purposes and continues to grow in importance for use in medical diagnosis and treatment, such as for diabetes, and in other diverse applications. In the medical field, it is desirable for lay operators to perform tests routinely, quickly, and reproducibly outside of a laboratory setting, with rapid results and a readout of the resulting test information. Testing can be performed on various bodily fluids and, for certain applications, is particularly related to the testing of blood and/or interstitial fluid. Performing home-based testing can be difficult for many patients, especially for patients with limited hand dexterity, such as the elderly or diabetics. For example, diabetics can sometimes experience numbness or tingling in their extremities, such as their hands, which can make self-testing difficult because they are unable to accurately position a test strip to collect the blood sample. In addition, wounds for diabetics tend to heal more slowly, and as a result, there is a desire to make incisions less invasive.

Recently, integrated lancing test strips have been developed in which a test strip is integrated with a lancet so as to form a single disposable unit. While these integrated units have somewhat simplified the collection and testing of fluid samples, there are still a number of issues that need to be resolved before a commercial unit can be implemented. One issue concerns maintaining the sterility of the lancet so as to minimize the risk of infection. In practice, conventional plastic or syringe type caps that are used to maintain the sterility of typical lancets cannot be incorporated with integrated lancing test strips for several reasons, especially for those designs with lancets that are moveable relative to the rest of the test strip. With typical syringe type caps, the cap encapsulates the lancet, and the cap is removed by pulling or twisting the cap off the lancet. However, the removal of the cap from the lancet without destroying or damaging the integrated device is difficult or even practically impossible. Moreover, automatic cap removal with such caps can be difficult. There is a trend to make lancets smaller or thinner so as to make less traumatic or less invasive incisions, which in turn makes self-monitoring less painful as well as promotes healing of the incision. However, due to their thinner nature, lancets are more prone to bending or are susceptible to other damage, especially when protective caps are removed. Further, the pulling or twisting action during cap removal can damage the test strip, like delicate electrodes in electrochemical type test strip, or can even result in the lancet being separated from the test strip.

Integrated devices have been proposed in which the lancet is encapsulated within a sterilized plastic body or a molded plastic plug that encloses one end of a lancet chamber. During lancing, the lancet pierces the body so as to extend from the body and lance the tissue. Such a design is suitable for automated systems because the lancet can be fired without the need to remove a protective cap. Given their bulky and rigid nature, these types of designs are not well suited for magazines, drums, cassettes, cartridges and the like, however. The encapsulating plastic creates a rather large profile, which does not allow a plurality of integrated devices to be packed in a tight package. Due to the somewhat rigid nature of the encapsulating material, the devices are too rigid by themselves for integration into a reel-to-reel type cassette design. Moreover, the injection molding required to manufacture these types of integrated devices can make the devices considerably more expensive as well as more difficult to assemble. Such designs can also limit how small the lancet can be because the lancet has to be rigid enough to still be able to puncture the seal.

Other integrated disposable designs have been proposed in which the entire unit is sealed within a protective packet. However, these designs require the entire disposable unit to be sterilized at the same time, which results in a whole host of difficulties. Unfortunately, sterilization techniques for lancets, such as radiation, adversely affect the chemical enzymes of the test strip. Hence, if left uncompensated, the accuracy of the test strip can be significantly hampered. To compensate for the changes that occur during sterilization, samples from sterilized lots are taken so that an adjustment or calibration value can be calculated for the lot. Before use, the calibration value for the lot is entered, either manually or automatically, into the meter to compensate for lot variations. Moreover, certain desirable sterilization techniques for lancets are impractical when the lancet and test strip are combined together because these techniques tend to damage or even destroy components on the test strip. In addition, undesirable cross contamination can occur between the lancet and the test strip when sealed in the same protective packet. For instance, components of the test strip, such as chemicals, biological components, adhesives and the like, can migrate within the packet onto the lancet, thereby possibly compromising the sterility of the lancet.

Ensuring that a sufficient amount of body fluid is collected during sampling is another issue that needs to be addressed before a viable commercial integrated lancing test strip can be implemented. It is desirable that the integrated device only lightly contacts the skin during fluid sampling. If the integrated device is pressed too hard against the skin, fluid flow from the incision can be blocked, which can occasionally lead to insufficient sample sizes. However, if the test strip is not touching at all, the test strip may be too far away for the blood drop to reach the capillary entrance of the test strip. When an insufficient amount of fluid for testing is collected, usually the integrated device has to be disposed of, and a new one is used to perform the test again. Further complicating this problem is that the elasticity of skin varies from person to person as well as varies between different body parts on the individual, which can create difficulties in locating the test strip. For example, the skin of a child is more elastic than that of the elderly. As a sampling device is pressed against the skin, the more elastic skin of the child tends to bow or pucker to a greater degree than the inelastic skin of the elderly. This variation of skin puckering height between individuals and body locations makes it difficult to design a meter that can accurately position a test strip so as to not contact the skin or only slightly contact the skin so as to not disturb fluid flow but still be able to contact the drop of fluid from the incision for fluid collection purposes.

Thus, needs remain for further contributions in this area of technology.

SUMMARY

One aspect concerns an integrated lancing test strip that includes a test strip adapted to analyze body fluid and a packet coupled to the test strip. The packet includes an incision forming member to form an incision in tissue. A sterility sheet covers the packet to maintain sterility of the incision forming member and prevents cross-contamination between the test strip and the incision forming member. The sterility sheet allows the incision forming member to be sterilized separately from the test strip.

Another aspect concerns a technique in which a lancet packet is created by enclosing a lancet in a sterility sheet to form a sterile enclosure. The lancet is sterilized, and the integrated lancing test strip is assembled by attaching the lancet packet to a test strip after sterilizing the lancet.

A further aspect relates to a meter that includes a holder that is configured to hold a test strip. An adjustment mechanism cooperates with the holder to position the test strip relative to the tissue with an incision for reducing pressure applied against the tissue. By reducing the pressure applied against the tissue, flow constriction of body fluid from the incision is minimized as the body fluid is collected with the test strip.

Another aspect concerns a lancet that defines an engagement opening and a firing mechanism to fire the lancet. The firing mechanism includes an engagement blade that is configured to engage with the engagement opening of the lancet. The engagement blade has one or more cutting edges. The engagement opening has one or more cut out portions at the cutting edges when the blade engages the engagement opening to minimize dulling of the cutting edge of the engagement blade.

A further aspect concerns a lancet. The lancet defines an engagement opening where the lancet is coupled to a firing mechanism. The engagement opening is shaped like a rounded diamond with circular cut outs at opposite ends of the diamond.

Still yet another aspect concerns an apparatus that includes a firing mechanism configured to fire a lancet that is sealed inside a lancet packet for cutting an incision in skin. The firing mechanism includes an engagement blade configured to engage the lancet. The engagement blade has a cutting edge positioned to form a slit in the lancet packet as the engagement blade actuates the lancet for providing smooth actuation of the lancet.

Other aspects concern an apparatus in which a lancet is sealed inside a lancet packet to maintain sterility of the lancet. A test strip is attached to the lancet packet. A firing mechanism includes an engagement blade configured to engage with the lancet. The firing mechanism is configured to pierce the lancet packet with the blade during firing of the lancet to minimize cross-contamination between the lancet and the test strip.

Further aspects concern a technique in which a blade of a firing mechanism engages with a lancet that is enclosed inside a packet. The blade includes a cutting edge. A slit is formed in the packet with the cutting edge of the blade by advancing the lancet with the blade to form an incision in skin.

Still yet a further aspect concerns a technique in which a lancet integrated test strip is loaded into a meter that includes a firing mechanism. The lancet integrated test strip includes a lancet sealed inside a lancet packet and a test strip attached to the lancet packet. The lancet is fired with the firing mechanism to cut an incision in skin. The cross-contamination risk between the lancet and the test strip is reduced by piercing the lancet packet during firing of the lancet. A body fluid sample from the incision is analyzed with the test strip.

Further forms, objects, features, aspects, benefits, advantages, and embodiments of the present invention will become apparent from a detailed description and drawings provided herewith.

DESCRIPTION OF THE SELECTED EMBODIMENTS

Figure 1:
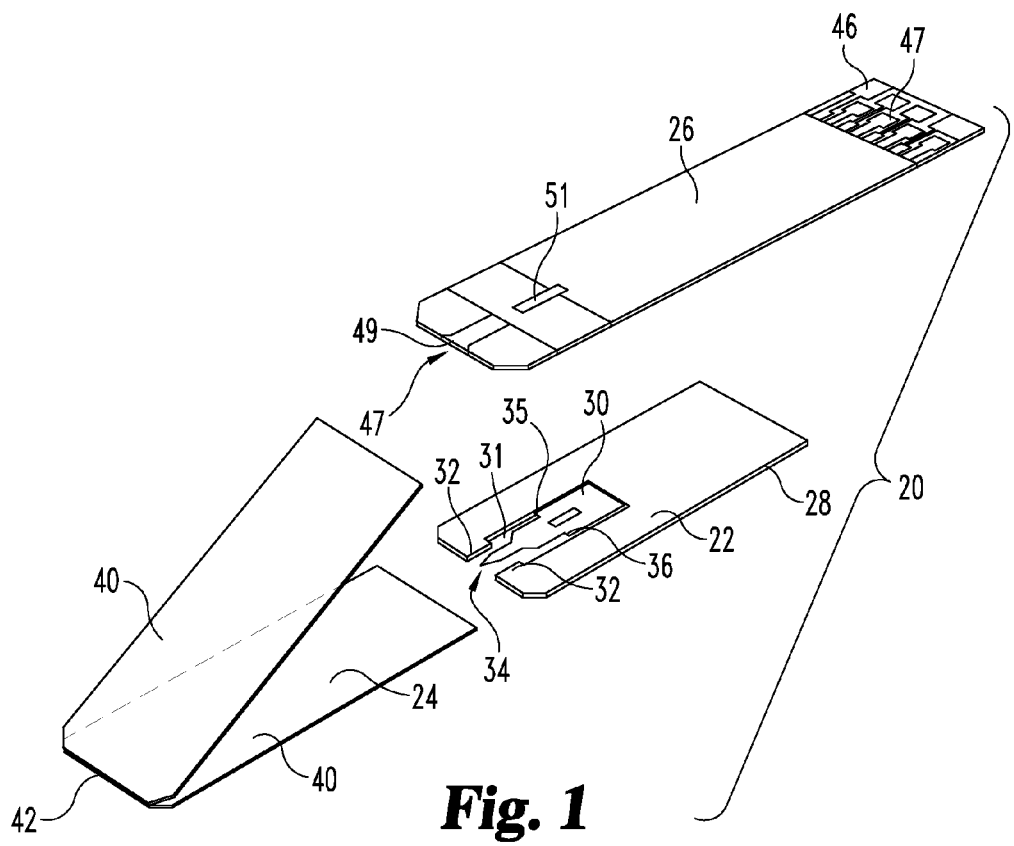
FIG. 1 is a first top exploded view of an integrated lancing test strip according to one embodiment.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates. One embodiment of the invention is shown in detail, although it will be apparent to those skilled in the relevant art that some features that are not relevant to the present invention may not be shown for the sake of clarity.

One of the many embodiments of the present invention concerns an integrated lancing test strip that includes a unique sterility enclosure system. The integrated lancing test strip includes a lancet for forming an incision that is attached to a test strip for analyzing fluid from the incision. The lancet is at least partially enclosed by a sterility sheet, which maintains sterility of the lancet and simplifies manufacturing of the integrated lancing test strip. By enclosing the lancet in the sterility sheet, the lancet can be sterilized separately from the test strip and then attached to the test strip after sterilization. As a result, this separate or modular construction of lancet and test strip allows the lancet to be sterilized without adversely effecting chemical enzymes in the test strip that would affect the accuracy of the test results. With the sterility sheet, the integrated lancing test strip can also have a compact profile, which is well suited for incorporation of multiple integrated lancing test strips into magazines, drums, cassettes, cartridges, and the like. Further, the sterility sheet minimizes cross-contamination between the lancet and the test strip before, during, and after use. In one form, the integrated lancing test strip is loaded into a lancing device or meter that is configured to fire the lancet. The meter includes an adjustment mechanism that allows the user to adjust the position of the test strip relative to the skin during sampling. The adjustment mechanism allows users to compensate for a number factors, such as variations in skin elasticity, skin type, body part size, and the pressure applied, to name a few. The adjustment mechanism can be used to compensate for these different conditions so as to allow the test strip to be positioned close enough to collect a fluid sample but not too close so as to hinder fluid flow from the wound.

An integrated lancing test strip or device 20 according to one embodiment, among many, of the present invention will be described initially with reference to FIGS. 1, 2, 3, 4, 5 and 6. Referring to FIG. 1, the integrated lancing test strip 20 includes a lancet assembly or incision forming member 22 for forming an incision in tissue, a sterility sheet or foil 24 for maintaining the sterility of the lancet 22, and a test strip 26 for acquiring a body fluid from the incision. Both the lancet 22 and the test strip 26 in the illustrated embodiment are generally flat such that the integrated lancing test strip 20 has an overall flat appearance. By being flat, multiple integrated lancing test strips 20 can be incorporated into magazines, cassettes, drums, cartridges, and the like, which allows a plurality of integrated lancing test strips 20 to be used without the need to individually load and/or dispose of used integrated devices 20. For example, the overall flat shape allows multiple integrated lancing test strips 20 to be stacked upon one another in a magazine or rolled around a reel in a cassette. Furthermore, the overall flat shape allows the integrated lancing test strip 20 to be manufactured with a continuous process in which layers of component materials can be layered to form contiguous strips of integrated lancing test strips 20 that can be cut to form individual units or remain attached for use in cassettes and the like. It should nonetheless be recognized that the integrated lancing test strip 20 in other embodiments can have a different overall shape.

Figure 5:
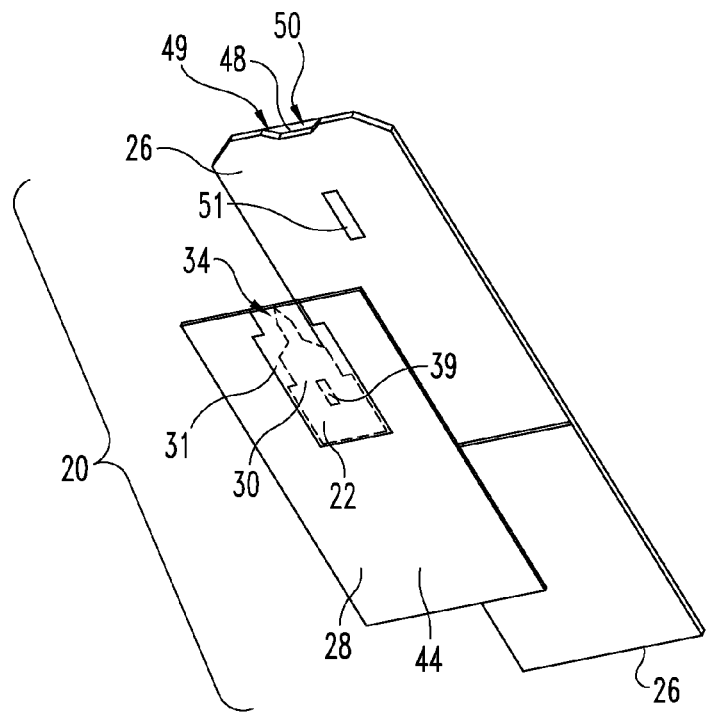
FIG. 5 is a bottom exploded view of the FIG. 1 integrated lancing test strip.

As can be seen in FIGS. 1 and 5, the lancet assembly 22 has a retaining element or guide member 28 that at least in part helps to guide a piercing member or lancet 30 during lancing. The lancet 30 is slidably retained within a guide slot or opening 31 that is defined in the retainer 28. In the course of lancing, the guide slot 31 guides the movement of the lancet 30 during both extension and retraction. In the illustrated embodiment, the lancet 30 and the retainer 28 are separate components that are not directly attached to one another. Nevertheless, in other embodiments, the lancet 30 and the retainer 28 can be connected to one another. For example, the lancet assembly 22 can have breakable tabs that connect the lancet 30 to the retainer 28 so that the lancet 30 is held in place during manufacturing as well as prior to lancing, thereby reducing the risk of injury. During lancing, the tabs are broken to allow the lancet 30 to extend from the integrated lancing test strip 20. In another example, a spring for retracting the lancet 30 connects the retainer 28 to the lancet 30.

Figure 7:
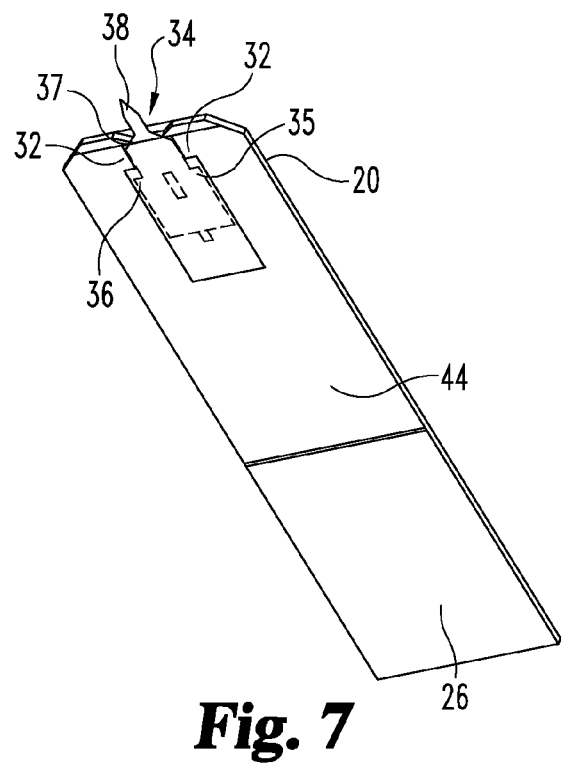
FIG. 7 is a second bottom perspective view of the FIG. 1 integrated lancing test strip with the lancet in the extended position.

As shown, end stops 32 of the retainer 28 extend inwardly at a slot opening 34 of the guide slot 31 so as to limit the movement of the lancet 30, thereby retaining the lancet 30 in the guide slot 31, as is depicted in FIG. 7. The lancet 30 has a body portion 35 with one or more stop edges 36, which are wider than the slot opening 34. When the lancet 30 is fully extended, the stop edges 36 of the lancet 30 can contact the end stops 32, and thus, limit the travel of the lancet 30. However, in other embodiments, the firing mechanism, which is used to fire the lancet 30, limits the travel of the lancet 30. A neck portion 37 of the lancet 30, which is slightly smaller that the size of the slot opening 34, extends from the body portion 35 of the lancet 30. During extension of the lancet 30, the neck 37 is received between the end stops 32 such that the end stops 32 can limit undesirable rotation of the lancet 30 as the tissue is punctured. It should be noted that the sterility sheet 24 helps to constrain out-of-plane rotation of the lancet. In one form, the lancet 30 is 1 mil thinner than the retainer 28 so as to minimize friction during actuation, but of course, the dimensions can vary in other embodiments. Extending from the neck 37, the lancet 30 has a blade portion or tip 38 that is configured to cut tissue. In the illustrated embodiment, the lancet defines an engagement notch or opening 39 for coupling the lancet 30 to a firing mechanism. In one form, the lancet assembly 22 is made at least in part of medical grade stainless steel, but it should be recognized that the lancet assembly 22 can be made of other materials, such as ceramics and/or plastics. Furthermore, it is contemplated that the guide member 28 and the lancet 30 can be made of different materials and/or manufactured separately. In one embodiment, the guide member 28 and lancet 30 are formed by a photo-etching technique in which a sheet of metal is photo-etched to form both the guide member 28 and the lancet 30, and in another embodiment, the lancet assembly 22 is manufactured via stamping. In another embodiment, the retainer 28 is stamped from a plastic sheet via a rotary die, and the lancet 30 is made from metal. The lancet assembly 22 in still other embodiments can be manufactured through other techniques as would occur to those skilled in the art.

Figure 2:
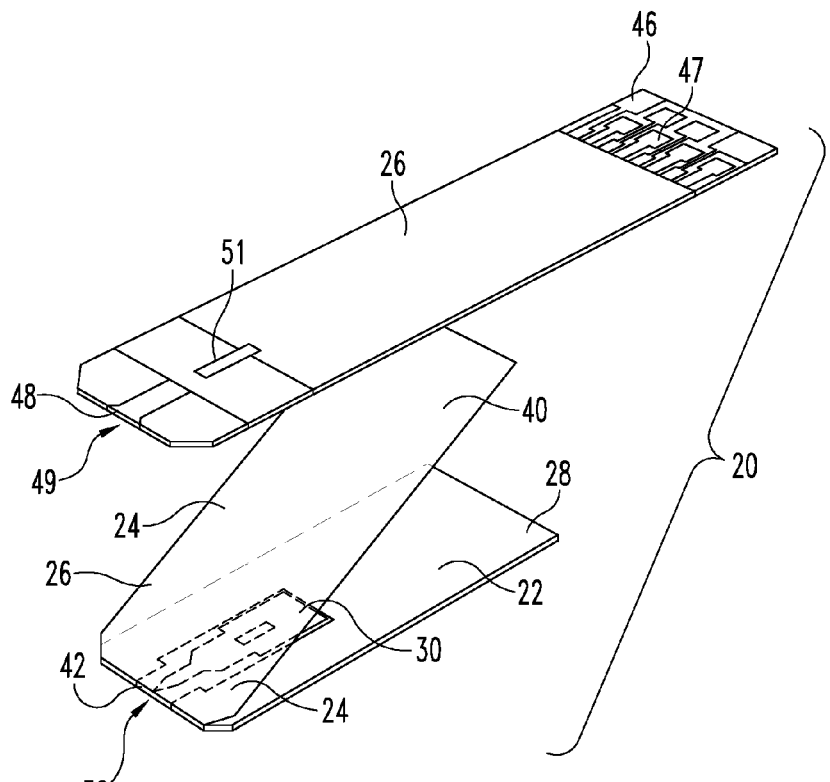
FIG. 2 is a second top exploded view of the FIG. 1 integrated lancing test strip.
Figure 3:
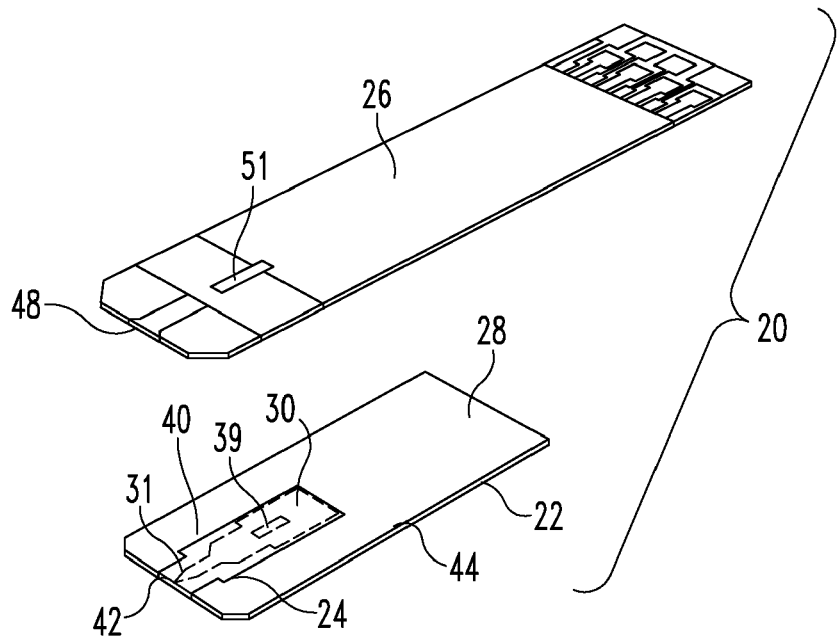
FIG. 3 is a third top exploded view of the FIG. 1 integrated lancing test strip.

With reference to FIGS. 1 and 2, after the lancet assembly 22 is formed, the lancet assembly 22 can be then packaged within the sterility sheet 24. As will be appreciated from the discussion below, the lancet assembly 22 can be packaged in the sterility sheet 24 before, during, or after the lancet assembly 22 is sterilized. In the illustrated embodiment, the sterility sheet 24 is a sheet of metallic foil, and in another embodiment, the sterility sheet 24 is made of plastic. In one particular form, the sterility sheet 24 is a 19-30 micron thick PET foil. It should be recognized that the sterility sheet 24 can be made of other types of materials and can have different dimensions. During manufacturing, the sterility sheet 24 is folded into two flaps 40 with a crease or fold 42 in between, as is shown in FIG. 1. After folding, the lancet assembly 22 in FIG. 2 is sandwiched between the two folds 40 such that the crease 42 closes the slot opening 34 of the guide slot 31. As depicted in FIG. 3, the folds 40 are secured to the opposite (flat) sides of the lancet assembly 22 so that the lancet 30 is sealed inside the guide slot 31 with the slot opening 34 closed by the crease 42. In one form, an adhesive is used to secure the sterility sheet to the guide member 28. Adhesive is applied on the guide member 28 around the guide slot 31 but is not applied to the lancet 30 so that the lancet 30 is able to still slide within the guide slot 31. Although an adhesive is used in the illustrated embodiment, it should be understood that the sterility sheet 24 can be sealed with the guide member 28 in other manners, such as through heat sealing. In the illustrated embodiment, the edges of the folds 40 are not sealed together, but it is envisioned that in other embodiments the edges of the sterility sheet 24 can be sealed together so as to form a pocket that encloses the entire lancet assembly 22. In still yet another embodiment, instead of folding the sterility sheet 24, two sterility sheets 24 are joined together with the lancet assembly 22 sandwiched in between. For the sake of clarity, the drawings only show how an individual integrated lancing test strip 20 is formed, but it is contemplated that the integrated lancing test strips 20 in one embodiment are formed in a continuous process. In the continuous process, the sterility sheet 24 is a continuous band that is rolled off a reel and folded around a continuous band or belt of lancet assemblies 22 that are likewise rolled from a reel. In one variation, the lancet assemblies are singulated from the reel before being sealed in place.

Once joined together, the lancet assembly 22 and the sterility sheet 24 form a lancet package or packet 44. As mentioned before, the lancet assembly 22 can be sterilized before being enclosed in the sterility sheet 24. The lancet assembly 22 can be sterilized through any number of sterilization techniques as would occur to those skilled in the art, such as through chemical, heat, and/or radiation sterilization techniques, to name a few. It should be understood that all or part of the lancet assembly 22 can be sterilized. For instance, only the lancet 30 and guide slot 31 can be sterilized, if so desired. In another embodiment, the lancet assembly 22 is sterilized after the lancet assembly 22 is packaged inside the lancet package 44. In one form, a radiation sterilization technique is used once the lancet 30 is enclosed by the sterility sheet 24. With the lancet package 44, sterilization of the lancet assembly 22 can occur without exposing the test strip to the undesirable effects of lancet sterilization.

In the illustrated embodiment, the test strip 26 is an electrochemical type test strip. In one particular form, the test strip 26 includes a modified version of an ACCU-CHEK® brand test strip (Roche Diagnostics GmbH), but it is envisioned that other types of test strips can be used. For example, the test strip 26 in other embodiments can include an optical type test strip or can analyze fluid samples in other manners. At one end, the test strip 26 in the illustrated embodiment includes a connection portion 46 with electrical contacts 47 that transmit sample readings to a meter. Opposite the connection portion 46, the test strip 26 has a capillary channel 48 with a capillary opening 49 that is configured to draw a body fluid sample from an incision formed by the lancet 30 via capillary action. As should be appreciated, the test strip 26 inside the capillary channel 48 includes an analysis region that includes electrodes, such as working, counter, and reference electrodes, and reagents for analyzing the fluid sample. In one form, the connection portion 46 is connected to a meter, and the sample readings from the electrodes in the analysis region are transmitted to the meter via the electrical contacts.

Figure 6:
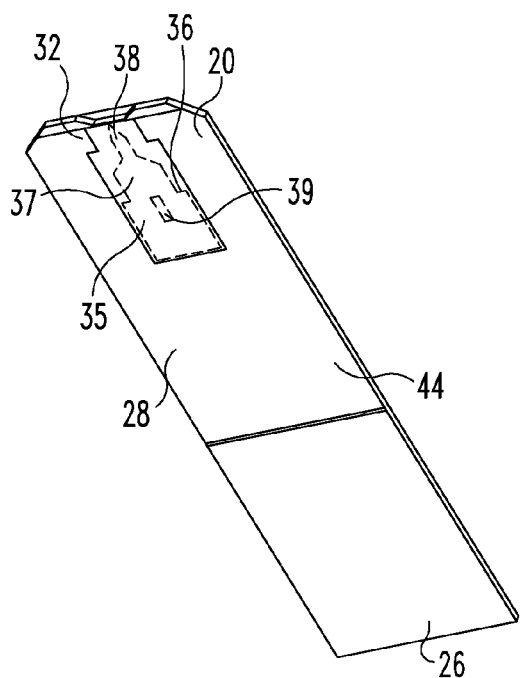
FIG. 6 is a first bottom perspective view of the FIG. 1 integrated lancing test strip with the lancet in a retracted position.

Looking at FIGS. 5 and 6, the sterilized lancet package 44 is attached to the test strip 26 to form the integrated lancing test strip 20. As depicted, the lancet package 44 is attached at the end of the test strip 26 proximal to the capillary opening 49 of the capillary channel 48. In particular, the guide slot opening 34 of the lancet assembly 22 and the capillary opening 49 of the test strip 26 are positioned near one another in a side-by-side relationship so that when the lancet 30 forms the incision, the capillary channel opening 49 is positioned in close proximity to collect the body fluid. The test strip 26 is attached to the exterior of the sterility sheet 24 enclosing the lancing member 22 to complete the integrated test strip 20. The test strip 26 in one form is attached to the lancet package 44 through an adhesive, but it should be recognized that the test strip 26 and lancet package 44 can be attached in other manners. In one form, the lancet package 44 is attached to the test strip 26 such that the end edges of both are aligned with another. However, in other embodiments the edges of the lancet package 44 and the test strip 26 can be offset from one another. For example, the edge of the lancet package 44 in the illustrated embodiment, as is demarked by crease 42, is recessed slightly from the edge of the test strip 26 at the capillary opening 49. By having the lancet package 44 recessed, fluid flow to the capillary channel opening 49 is promoted and body fluid is directed away from the lancet package 44. In another example, the sterility sheet 24 is positioned such that the crease 42 extends past the edge of the test strip 26. With this example, all or part of the sterility sheet 24 can be hydrophobic and/or hydrophilic so as to direct fluid flow towards the capillary channel 48. In one particular form, the sterility sheet 24 extends from the test strip 26 such that the sterility sheet 24 acts like a flexible wicking flag that draws fluid into the capillary channel 48.

To draw the body fluid towards the capillary channel opening 49 and away from the lancet 30, the test strip 26 in the illustrated embodiment has a fluid direction notch 50 facing the lancet package 44. In order to enhance fluid flow towards the capillary channel opening 49, the sterility sheet 24 can be treated and/or made to be hydrophobic. With the sterility sheet 24 being hydrophobic, the sterility sheet can squeegee or wipe body fluid from the lancet 30 as the lancet 30 retracts back inside the guide slot 31. It is thought that the wiping action of the sterility sheet 24 increases the amount of body fluid available for sampling as well as makes the lancet 30 cleaner for disposal purposes. As noted before, with the lancet 30 sealed in the lancet package 44, the risk of cross-contamination between the lancet 30 and the test strip 26 is reduced.

Figure 4:
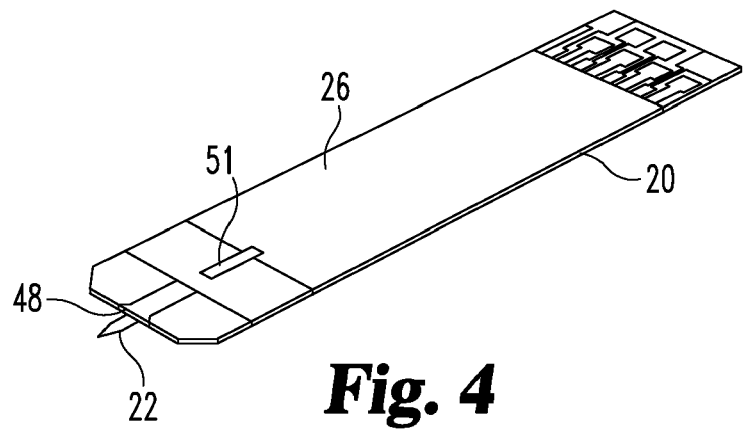
FIG. 4 is a top perspective view of the FIG. 1 integrated lancing test strip with its lancet in an extended position.

In FIGS. 3 and 4, the test strip 26 further defines a relief slot 51 through which a blade tip of a cam arm extends when engaging the lancet 30 during loading and firing. In addition, the relief slot 51 can be used to vent air from the capillary channel 48 as fluid is collected. The length of the relief slot 51 generally approximates the length of the lancing stroke of the firing mechanism used to actuate the lancet 30. When the lancet package 44 is attached to the test strip 26, the engagement notch 39 on the lancet 30 is aligned with the relief slot 51 in the test strip 26. As will be described in greater detail below, the blade tip of a cam arm for the firing mechanism extends through the engagement notch 39 of the lancet 30 as well as into the relief slot 51. When doing so, the blade tip pierces the sterility sheet 24. During lancing, the cam arm via the blade extends and retracts the lancet 30 relative to the test strip 26. As the lancet 30 extends, the tip 38 of the lancet 30 pierces the sterility sheet 24 at crease 42, as is illustrated in FIGS. 4 and 7. In one form, the sterility sheet 24 at the crease 42 is weakened so as to aid in puncturing by the lancet 30, but in other forms, the crease 42 is not weakened. Once the lancet 30 is retracted back inside the guide slot 31, as is shown in FIG. 6, the two flaps 40 of the sterility sheet 24 can hold the lancet 30 inside through friction. By engaging the lancet 30 in such a manner, the risk of accidental puncturing by the integrated lancing test strip 20 is reduced because it is more difficult to manually and/or accidentally actuate the lancet 30. It should be recognized that the lancet assembly 22 can incorporate other structures for engaging the lancet 30. For instance, the engagement notch 39 in the lancet 30 can be replaced with a protrusion or knob. It is also contemplated that the lancet can be fired through non-mechanical and/or non-contact techniques, which do not require the puncturing of the sterility sheet 24. As an example, the lancet 30 in another embodiment is magnetized and fired magnetically through a voice coil driver. With the lancet 30 enclosed in the sterility sheet 24 both before and after lancing, the risk of contamination is reduced, and the risk of accidental injury is likewise reduced.

Figure 8:
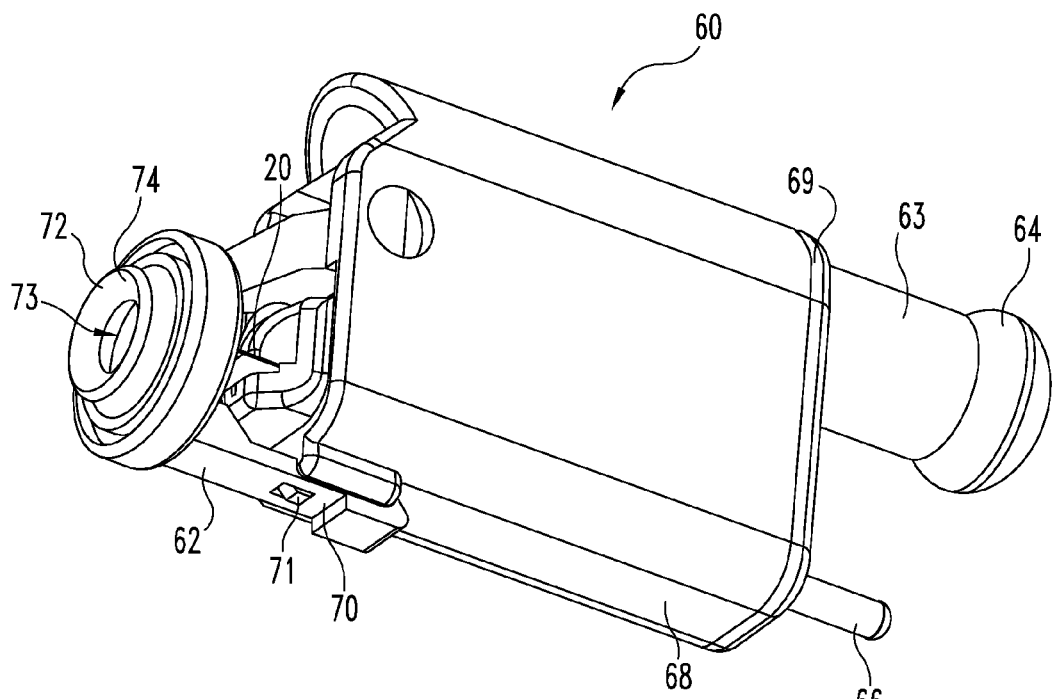
FIG. 8 is a first front perspective view of a meter when the FIG. 1 integrated lancing test strip is loaded.
Figure 9:
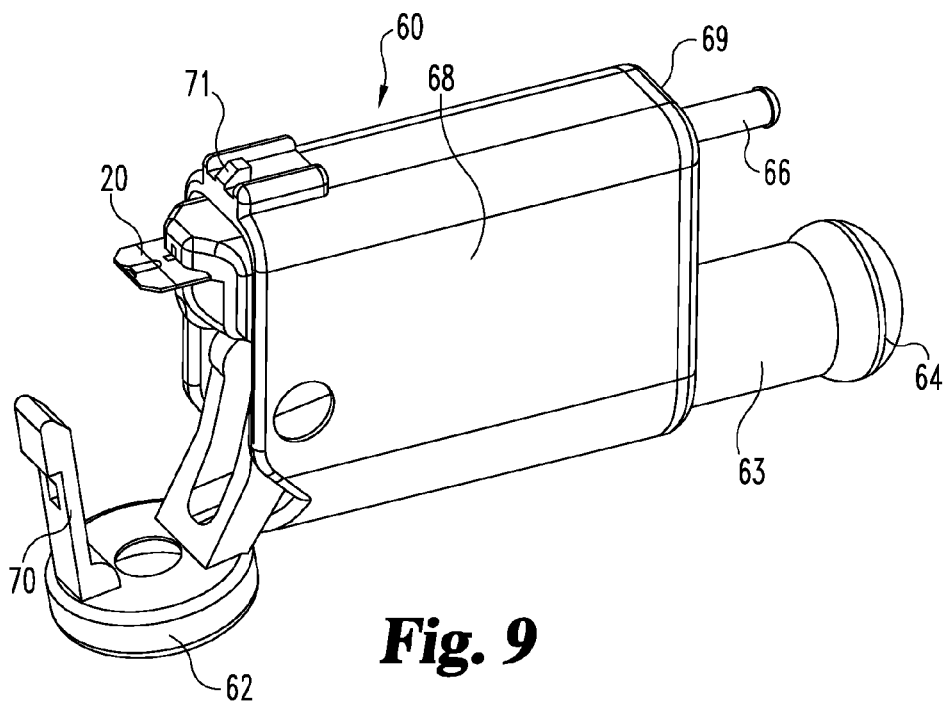
FIG. 9 is a second front perspective view of the FIG. 8 meter during loading of the FIG. 1 integrated lancing test strip.
Figure 10:
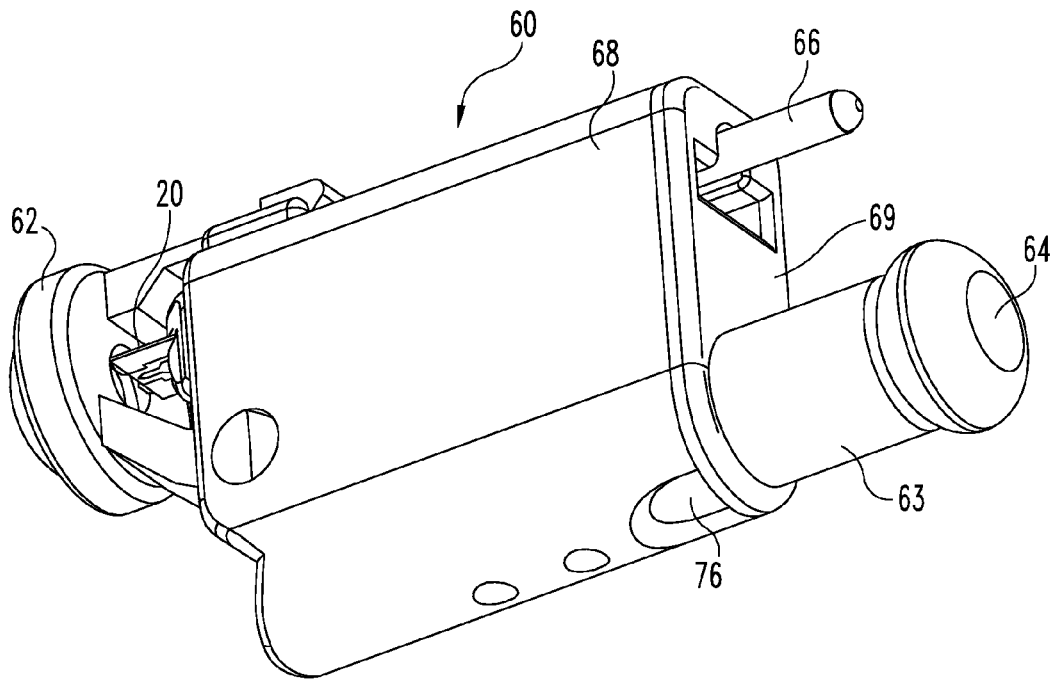
FIG. 10 is a rear perspective view of the FIG. 8 meter.

A lancing device or meter 60, according to one embodiment, that is configured to lance tissue and collect as well as analyze fluid from the tissue with the integrated lancing test strip device 20 is illustrated in FIGS. 8, 9 and 10. In one embodiment, the meter 60 includes a display or other types of output means for outputting sample readings from the integrated lancing test strip 20. The meter 60 in the illustrated embodiment is configured to adjust the relative position of the test strip 26 from the skin during sampling. Referring to FIG. 8, the lancing device 60 has a cap portion 62 that is configured to contact tissue and a firing mechanism 63 with a cocking knob 64 for the cocking of the firing mechanism 63. The lancing device 60 further includes an adjustment control or mechanism 66 for adjusting the sampling position of the test strip 26 and a housing 68 with an end plate 69 that houses the components of the lancing device 60. As shown in FIGS. 8 and 9, the cap 62 is hingedly coupled to the housing 68 so that the cap 62 can be pivoted away to permit loading of the integrated lancing test strip 20 (FIG. 9). The cap 62 further includes a latch 70 with an opening that engages a lock tab 71 on the housing 68 such that the cap 62 is locked in place once the integrated lancing test strip 20 is loaded, as is depicted in FIG. 8. An expression member 72 is coupled to the cap 62, and the expression member 72 defines a sampling opening 73 through which the lancet 30 lances the skin and the test strip 26 collects fluid from the incision. In the embodiment shown, the expression member 72 is ring-shaped and is threadedly coupled to the cap 62, so that the expression member 72 is able to move in a telescoping fashion, thereby allowing height adjustment of the expression member 72 relative to the cap 62. The proximity of the test strip 26 to the target tissue can be adjusted by the user, by turning the expression member 72. This adjustment can be individually based on a number of factors such as the size of the body part being sampled and how hard the user typically presses against the skin. Around the sampling opening 73, the expression member 72 has a skin or tissue contacting surface 74 that is configured to contact the skin during lancing and sampling. In the illustrated embodiment, the skin contacting surface 74 is inwardly angled so as to promote expression of fluid from the incision as the cap 62 is pressed against the skin.

As can be seen in FIG. 10, the firing mechanism 63 includes a firing button 76 that is pressed by the user in order to actuate the firing mechanism 63, once cocked. In the illustrated embodiment, the firing mechanism 63 includes a spring-powered type firing mechanism of the type as generally known to those skilled in the art. To cock the firing mechanism 63 in one embodiment, the cocking knob 64 is rotated and the potential energy from rotating the knob 64 is stored by a torsion spring in the firing mechanism 63. In another embodiment, the cocking knob 64 is pulled and the potential energy from pulling the knob 64 is stored by one or more springs in the firing mechanism 63. When the user presses the firing button 76, the potential energy stored in the springs is released so that the energy is used to fire the lancet 30. After the lancet 30 is fully extended, the firing mechanism 63 recoils so as to retract the lancet 30 from the target tissue. It should be recognized that the lancing device 60 can incorporate other types of firing mechanisms as known to those skilled in the art, like electrical and/or pneumatic type firing mechanisms, for example.

Figure 11:
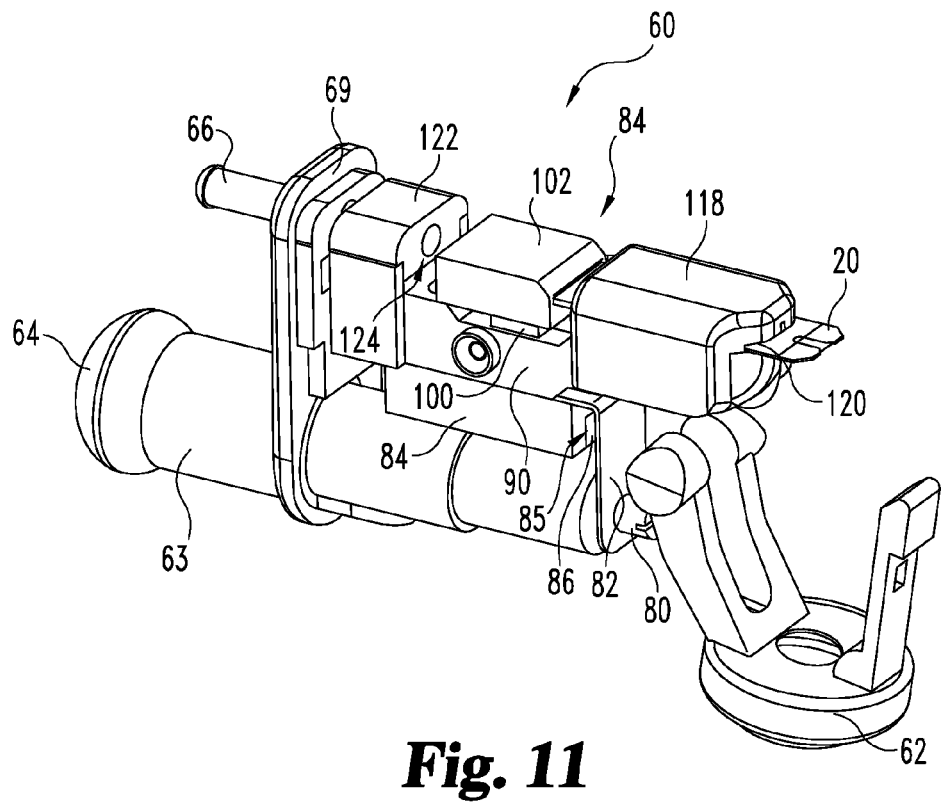
FIG. 11 is a perspective view of the FIG. 8 meter with its housing removed.
Figure 12:
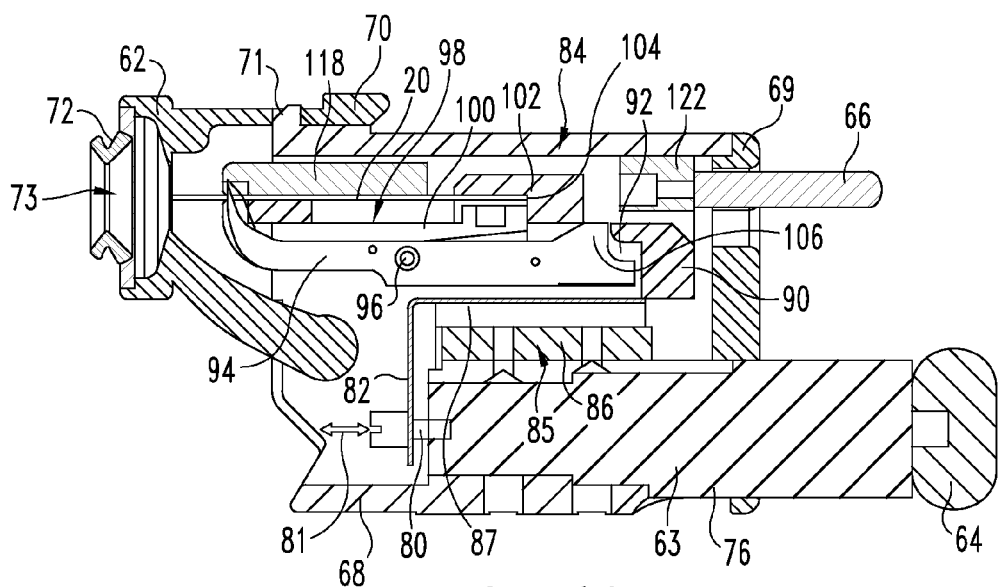
FIG. 12 is a cross-sectional view of the FIG. 8 meter.

FIG. 11 shows the lancing device 60 with the housing 68 partially removed, and FIG. 12 shows a cross-sectional view of the lancing device 60. As shown, the firing mechanism 63 extends through and is secured to the end plate 69 of the housing 68. Opposite the cocking knob 64, the firing mechanism 63 has an actuation arm 80 that is configured to extend from the firing mechanism 63 upon lancing and subsequently retract, as is indicated by double arrow 81. In the illustrated embodiment, the actuation arm 80 is in the form of a rod, but the actuation arm 80 as well as the rest of the firing mechanism 63 in other embodiments can have a different shape than is shown. To give the lancing device 60 a compact configuration, the lancing device 60 includes a drive connector 82 that is connected to the actuation arm 80 of the firing mechanism 63. The drive connector 82 is configured to transmit force from the firing mechanism 63 to an actuation assembly 84, which physically fires the integrated lancing test strip 20. In the illustrated embodiment, the drive connector 82 is L-shaped so that the firing mechanism 63 and the actuation assembly 84 can be oriented in a side-by-side relationship so as to give the lancing device 60 an overall compact shape.

The actuation assembly 84 includes a bearing block 87 with a bearing channel 85 that receives a bearing rib 86. The bearing block 87 is connected to the drive connector 82, and the bearing rib 86 is secured to the housing 86 via the firing mechanism 63. As the actuation arm 80 of the firing mechanism 63 extends and retracts, the bearing block 87 slides relative to the bearing rib 86.

Figure 13:
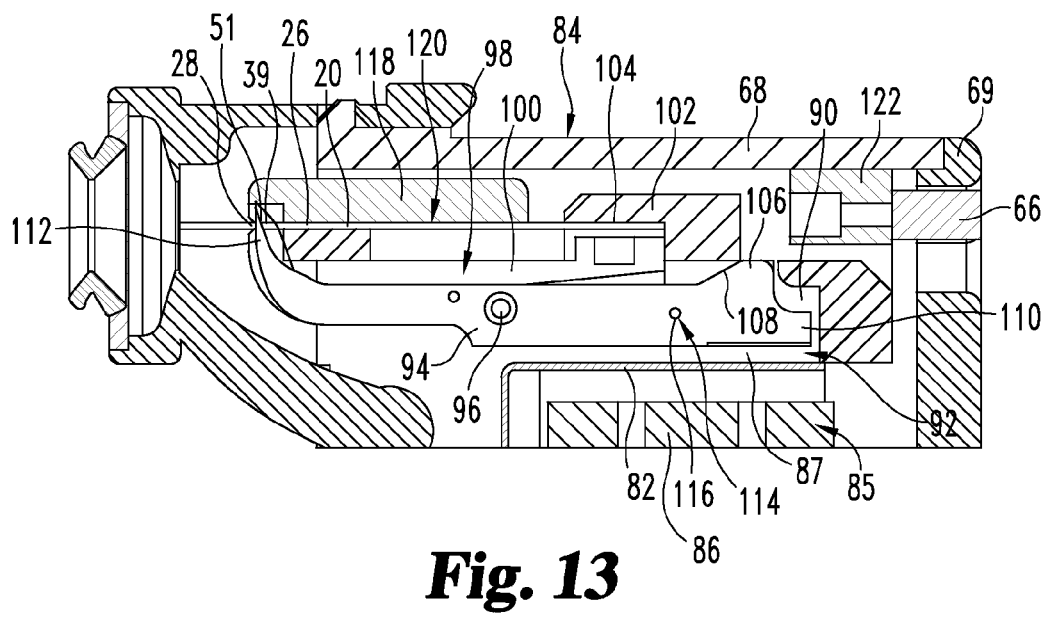
FIG. 13 is an enlarged cross-sectional view of an actuation mechanism in the FIG. 8 meter.

With reference to FIGS. 12 and 13, the actuation assembly 84 includes a strip holder 90 for holding and actuating the integrated lancing test strip 20. The strip holder 90 defines a cam arm channel 92 in which a cam arm 94 is pivotally disposed. As depicted, the cam arm 94 is pivotally coupled to the holder 90 via a pivot pin 96, but it should be realized that the cam arm 94 and the holder 90 can be pivotally coupled in other manners. Looking at FIG. 13, the holder 90 further defines a slide connector arm cavity 98 in which a connector arm 100 is slidably disposed. Connector arm 100 is connected to a connector block or member 102 such that the connector block 102 is able to slide relative to the holder 90. The connector block 102 defines a connector slot 104 that is shaped to receive the connection portion 46 of the test strip 26. Inside the connector slot 104, the connector block 102 in one form includes electrical contacts that touch the contacts 47 on the test strip 26 in order to transmit readings from the test strip 26 to the meter 60.

At one end, the cam arm 94 has a cam member or portion 106 with a cam surface 108 that is angled or tapered to engage the connector block 102. Near the cam portion 106, the cam arm 94 has a limit tab 110 that is configured to contact the holder 90 in order to limit the rotation of the cam arm 94. Opposite the cam portion 106, the cam arm 94 has a lancet engagement blade 112 that is sharp in order to pierce the sterility sheet 24 of the integrated lancing test strip 20. During loading of the integrated lancing test strip 20, the connector block 102 is pushed further inside the lancing device 60 towards the cam portion 106 of the cam arm 94. When the connector block 102 engages the cam surface 108 of the cam portion 106, the cam arm 94 is rotated such that the blade 112 punctures the sterility sheet 24. After cutting the sterility sheet 24, the blade 112 extends into the engagement notch 39 of the lancet 30 so that the cam arm 94 is able to hold the lancet 30 during lancing. The relief notch 51 in the test strip 26 ensures that the blade 112 extends completely through the engagement notch 39 so that the cam arm 94 fully engages the lancet 30. In the illustrated embodiment, the integrated lancing test strip 20 is loaded with the lancet assembly 22 facing the blade 112 so that the blade 112 first extends through the engagement notch 39 of the lancet 30 before extending through the relief notch 51 of the test strip 26. It is contemplated that in other embodiments the integrated lancing test strip 20 is flipped so as to be oriented in the opposite manner. That is, the test strip 26 faces the blade 112 during loading so that the blade engages the lancet 30 by extending first through the relief notch 51 in the test strip 26. In the illustrated embodiment, the holder 90 has one or more detent mechanisms 114 that engage one or more detent openings 116 in the cam arm 94 so as to hold the cam arm 94 in position during lancing. In one embodiment, the detent mechanism 114 includes a ball-type detent, but as should be recognized, other types of mechanisms can be used to hold the cam arm 94 in position. In the illustrated embodiment, the blade 112 is hooked shaped or angled so as to permit easy removal of the integrated lancing test strip 20 subsequent to sampling and/or testing. Near the blade 112, a cover 118 is secured to the holder 90. Together, the cover 118 and the holder 90 define a strip holder slot 120 that receives and holds the integrated lancing test strip 20 during both lancing and sampling. Referring again to FIG. 12, the strip holder slot 120 is aligned with the sampling opening 73 in the cap 62 so that the integrated lancing test strip 20 is able to sample fluid in an unencumbered manner.

As mentioned before, the adjustment control 66 in one form allows for the adjustment of the position of the test strip 26 relative to the skin during sampling so that the test strip 26 does not press too hard against the skin so as to constrict bleeding from the incision. Alternatively or additionally, the adjustment control 66 can be used for penetration depth control by limiting the amount of travel of the test strip 26 during firing, and a concentric return spring can be used to return the connector arm 100 and the connector block 102 to their initial position after the lancing cycle. As illustrated in FIGS. 11 and 12, the adjustment control 66 is threadedly secured to the end plate 69, and the adjustment control 66 extends through the end plate 69 and engages a limit stop 122, which faces the connector block 102. At least a portion of the stop 122 is received in a guide channel 124 (FIG. 11) so as to prevent rotation of the stop 122 as the adjustment control 66 is turned. By twisting the adjustment control 66, the distance between the stop 122 and the connector block 102 can be increased or reduced by a threaded rod connected in between. During operation, the stop 122 limits the travel of the connector block 102, which in turn limits how far the test strip 26 is able to retract away from the target tissue, and hence, control the distance between the capillary opening 49 of the test strip 26 and the surface of the target tissue. As a result, the test strip 26 can be kept in close proximity to the tissue or slightly contact the tissue without the risk of hindering blood flow from the wound. It is contemplated that the adjustment mechanism 66 can include other types of adjustment mechanisms. By way of a non-limiting example, the adjustment mechanism in another form can include an electrical motor that moves the stop 122. The position of the stop 122 can be adjusted manually by the user through one or more buttons on the meter 60 or can be automatically adjusted by the meter 60. In one form, the meter 60 automatically adjusts the position of the test strip 26 by sensing the relative position of the skin via a sonar-type detector and/or via an optical sensor. The expression member 72 in still yet another form is rotated in order to extend or retract the expression member 72, thereby adjusting the penetration depth of the lancet 30.

The integrated lancing test strip 20 can form an incision and collect body fluid from the incision using a number of techniques. In one technique, the test strip 26 is held fixed in relation to the lancing device 60, and the lancet 30 is moved forward and backward to pierce the skin. In another technique, the lancet 30 is held fixed to the test strip holder 90 while the test strip 26 can move with the connector block 102. When the test strip 26 contacts the skin, the test strip 26 is pushed back by the skin such that the lancet 30 is exposed so as to pierce the skin or other tissue. With the test strip 26 contacting the skin, variations in skin height do not significantly affect the penetration depth of the lancet 30.

Figure 14:
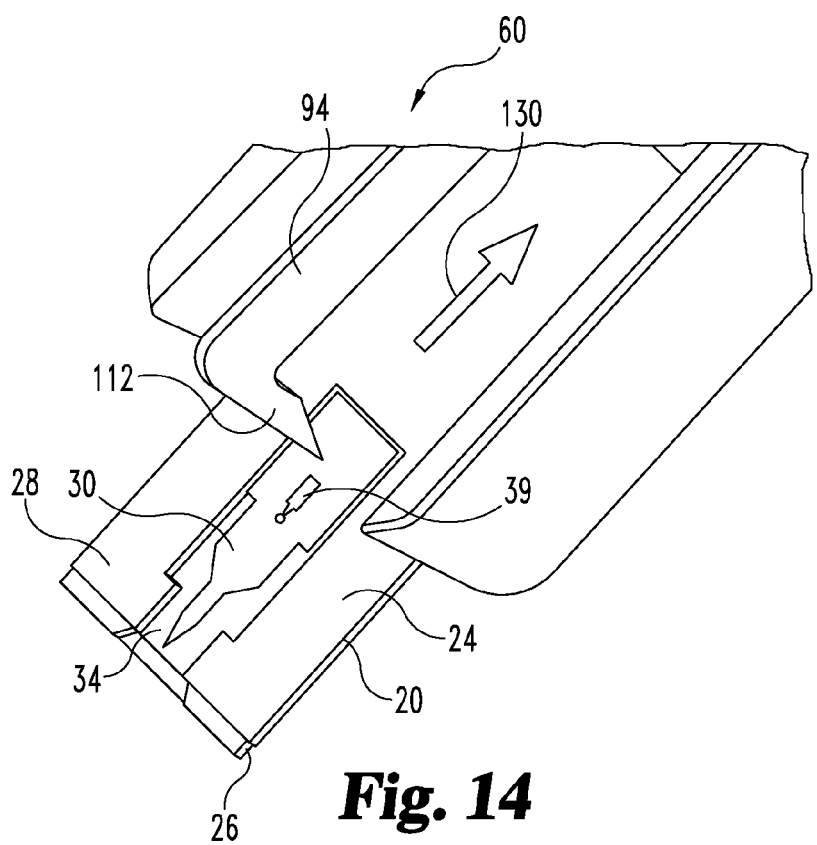
FIG. 14 is a perspective view of the FIG. 8 meter as the FIG. 1 integrated lancing test strip is loaded.
Figure 15:
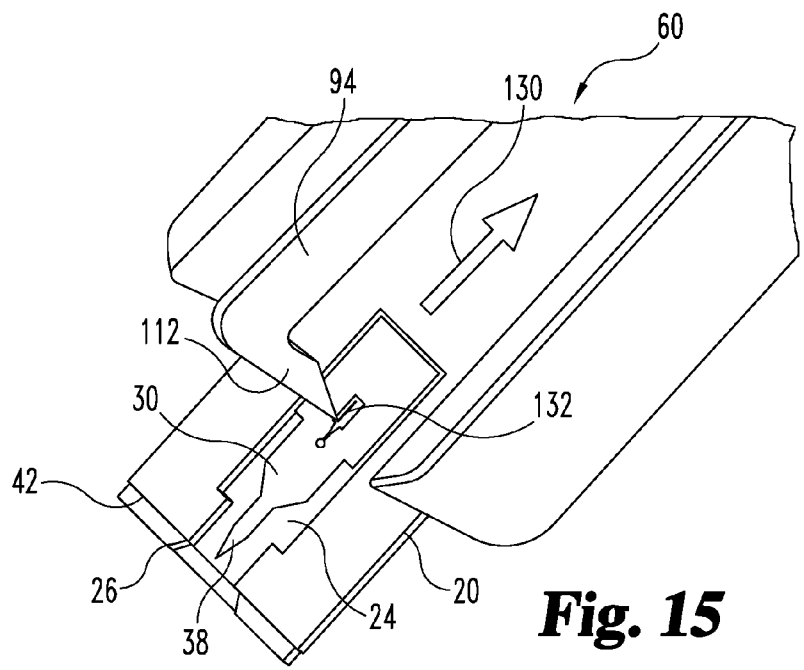
FIG. 15 is a perspective view of a cam arm of the FIG. 8 meter engaging the FIG. 1 integrated lancing test strip.

To aid in understanding and appreciating the features of the integrated lancing test strip 20 and the meter 60, a technique for sampling fluid will be described with reference to FIGS. 14, 15, 16, 17 and 18. From the previous discussion, it however should be recognized that the body fluid can be sampled in other manners. With reference to FIG. 14, the integrated lancing test strip 20 is loaded by pushing the integrated lancing test strip 20 into the meter 60, as is shown by direction arrow 130. The connection portion 46 of the test strip 26 is received in the connector block 102, as is depicted in FIG. 13. While the integrated lancing test strip 20 is pushed farther inside the meter 60, the connector block 102 engages the cam surface 108 on the cam arm 94 such that the cam arm 94 pivots in a teeter-totter fashion. The pivoting of the cam arm 94 causes the blade 112 on the cam arm 94 to pierce the sterility sheet 24 on the integrated lancing test strip 20 so that the blade 112 engages the engagement notch 39 in the lancet 30, as is depicted in FIG. 15. Once the cam arm 94 is rotated to engage the lancet 30, the detent mechanism 114 locks the position of the cam arm 94 so as to prevent accidental disengagement during lancing. While the integrated lancing test strip 20 is pushed farther inside the meter 60 (FIG. 15), as indicated by direction arrow 130, the blade 112 on the cam arm 94 forms a slit 132 in the sterility sheet 24. The slit 132 in the sterility sheet 24 allows for smooth movement of the lancet 30 and cam arm 94 during retraction. Once the connector 102 contacts the stop 122, the integrated lancing test strip 20 is fully loaded.

Figure 16:
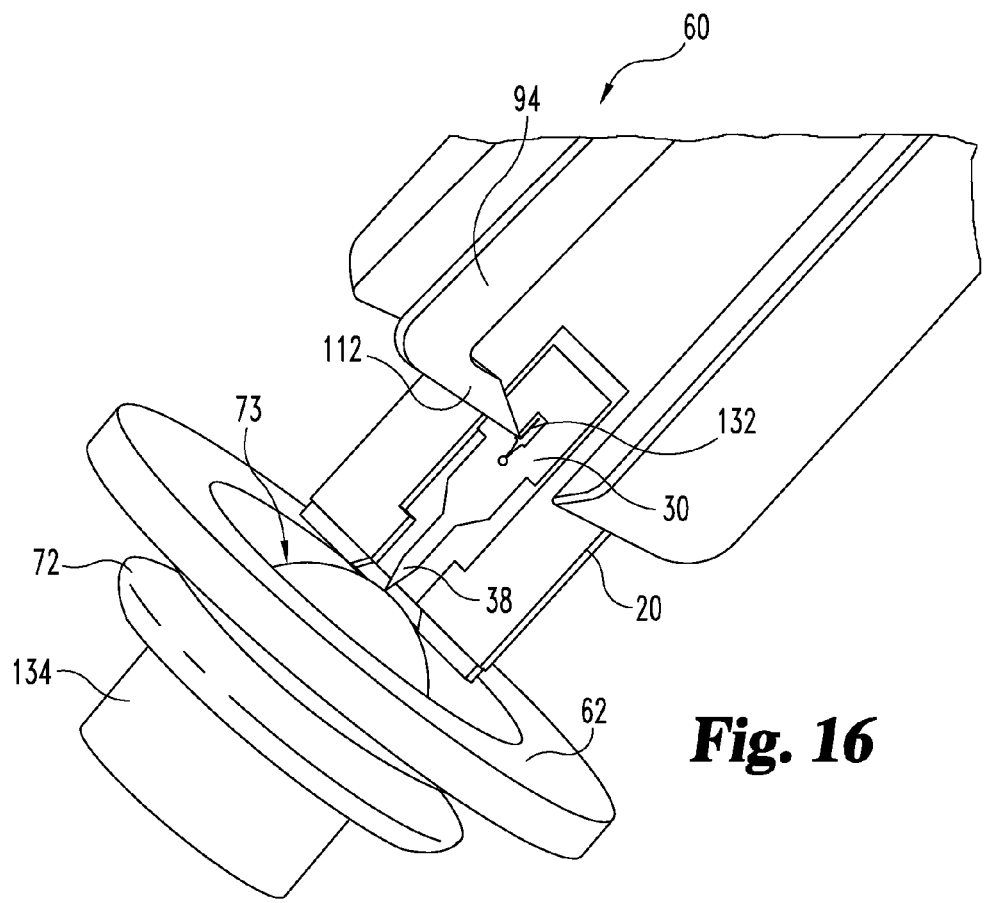
FIG. 16 is a perspective view of the FIG. 8 meter and the FIG. 1 integrated lancing test strip prior to lancing.

In one embodiment, when the integrated lancing test strip 20 is fully loaded, the lancet 30 remains completely sealed inside the pouch formed by the sterility sheet 24 until lancing is initiated. In another embodiment, like the one shown in FIG. 15, the tip 38 of the lancet 30 slightly pierces the crease 42 of the sterility sheet 24 once the integrated lancing test strip 20 is fully loaded. To prevent accidental injury, the tip 38 of the lancet 30 does not however extend past the edge of the test strip 26. During loading of the meter 60, the cap 62 of the meter 60 is pivoted out of the way in the manner as is shown in FIG. 9. Once loaded, the cap 62 of the meter 60 is rotated and locked into a firing position, like is illustrated in FIG. 8. In one embodiment, the firing mechanism 63 is cocked by twisting the knob 64, and in another embodiment, the firing mechanism 63 is cocked by pulling the knob 64. Before lancing is initiated, the sampling opening 73 of the cap 62 is positioned over a targeted body part or tissue 134, such as the skin of a finger, which is shown in FIG. 16, so that the expression member 72 contacts the body part 134. It should be recognized that the firing mechanism 63 can be cocked before or after the meter 60 is placed against the targeted body part 134.

Figure 17:
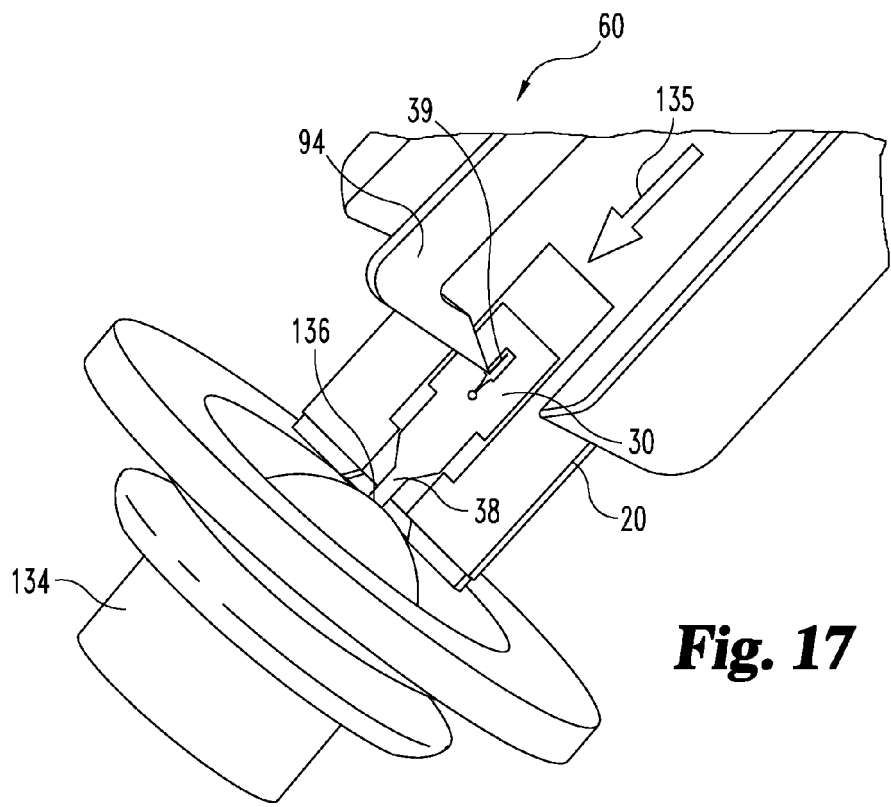
FIG. 17 is a perspective view of the FIG. 8 meter and the FIG. 1 integrated lancing test strip during lancing.

Referring to FIGS. 10, 12 and 17, the user presses the firing button 76 of the firing mechanism 63 to initiate lancing. Upon firing, the actuation arm 80 (FIG. 12) extends from the firing mechanism 63, and the drive connector 82 transmits this extension force to the holder 90, whereby the holder 90 likewise moves towards the body part 134. As the holder 90 moves, the integrated lancing test strip 20 also moves. Since the cam arm 94 is attached to the holder 90 and the blade 112 of the cam arm 94 is secured to the lancet 30, the lancet 30 extends along with the rest of the integrated lancing test strip 20 towards the body part 134. Once the test strip 20 contacts the body part 134, the frictional forces that caused the test strip 26 to move with the holder 90 are unable to move the test strip 26 any further so that the test strip 26 rests against the tissue 134. Although the test strip 26 stops moving, the lancet 30 continues to move because of the engagement of the lancet 30 with the cam arm 94 of the still moving holder 90. Consequently, upon contacting the tissue 134, the test strip 26 is pushed back, and the tip 38 of the lancet 30 is exposed such that the tip 38 penetrates the tissue 134, as is depicted in FIG. 17. As indicated by direction arrow 135 in FIG. 17, the lancet 30 continues to extend until the firing mechanism 63 reaches its maximum stroke length. After forming an incision 136 in the tissue 134, a spring that rests against the connector block 102 of the firing mechanism 63 retracts the holder 90, which in turn retracts the lancet 30 as well as the rest of the integrated lancing test strip 20 to its initial position. In another embodiment, the test strip 26 does not contact the skin during lancing, but rather, the tip 38 of the lancet is exposed by contacting the backside of the expression member 72.

Figure 18:
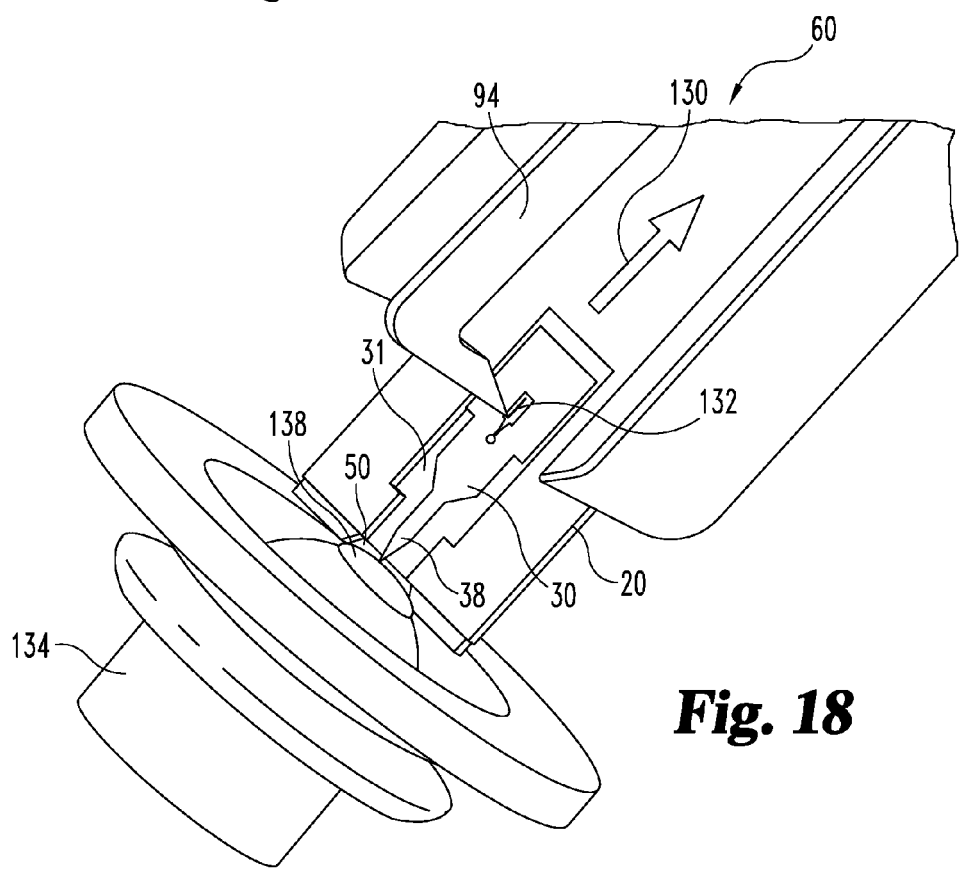
FIG. 18 is a perspective view of the FIG. 8 meter and the FIG. 1 integrated lancing test strip during sampling.

As mentioned previously, the adjustment control 66 via the stop 122 in conjunction with the expression cap 72 controls the position of the test strip 26 relative to the tissue 134 so as to prevent constriction of fluid flow from the incision 136. During retraction of the holder 90, the integrated lancing test strip 20 along with the connector block 102 retract until the connector block 102 contacts the stop 122, thereby limiting the retraction of the test strip 26. Although the test strip 26 stops retracting, the cam arm 94 along with the lancet 30 continues to retract in direction 130, as is shown in FIG. 18, such that the lancet 30 retracts inside the guide slot 31 of the lancet assembly 22. Once retracted, the lancet 30 can be received inside the sterility sheet 24 so as to reduce the risk of accidental injury as well as biological contaminate exposure during disposal. In one form, the sterility sheet 24 can act like wiper blades so as to wipe body fluid 138 or other contaminants from the lancet 30 so that the integrated lancing test strip 20 is generally cleaner after use as well as to increase the amount of body fluid 138 that is available for testing. In one example, the sterility sheet 24 is hydrophobic to enhance the ability to wipe body fluid 138 from the lancet 30.

Looking at FIG. 18, the edge of the test strip 26 is spaced slightly away from the surface of the tissue 134 but is still positioned close enough to collect the body fluid 138 from the incision 136. It should be noted that the user can twist the adjustment control 66 so that the integrated lancing test strip 20 lightly contacts the tissue 134 during sampling or space the test strip 26 farther away, if so desired. Moreover, it is envisioned that other components, such as bendable wicking flags and the like, can also contact the skin during sampling. The lancet 30 is recessed behind capillary opening 49 so the lancet 30 does not contact the tissue 134 when the lancet 30 is retracted and is far enough behind capillary opening 49 so the drop of body fluid 138 will find the capillary opening 49 of the test strip 26 before the body fluid 138 finds the opening formed by the lancet 30 in the sterility sheet 24. For instance, the lancet 30 in one embodiment is retracted 0.5 to 0.75 mm behind the capillary opening 49, and in another embodiment, the lancet 30 is retracted 1 mm behind the capillary opening 49. By recessing the lancet package 44 in the manner illustrated, expression of body fluid 138 from the incision 136 is not hindered by the presence of the lancet 30. If needed, the user can press the meter 60 against the tissue 134 such that the expression member 72 expresses the body fluid 138 from the incision 136. Once the body fluid 138 starts flowing from the incision 136, the capillary channel 48 of the test strip 26 collects the fluid 138. As previously noted, the test strip 26 has the notch 50 that directs the fluid flow towards the opening 39 of the capillary channel 48 and away from the lancet 30.

After a sufficient amount of the body fluid 138 is collected, the fluid 138 is analyzed with the test strip 26, and the test results are shown on a display on the meter 60 and/or transmitted to another device, like a computer, for further analysis. Once the integrated lancing test strip 20 has been used, the integrated strip 20 is removed from the meter 60 for disposal. During removal of the integrated lancing test strip 20, the cap 62 is pivoted out of the way to allow the user to gain access to the integrated lancing test strip 20, as is depicted in FIG. 9. To remove the integrated strip 20, the user pulls the integrated strip 20 out of the meter 60. With reference to FIG. 13, as the user pulls the integrated strip 20, the hooked or angled shape of the blade 112 causes the cam arm 94 to rotate away from the integrated lancing test strip 20. This rotational movement causes the cam arm 94 to disengage from the detent mechanism 114, thereby allowing the cam arm 94 to rotate freely. When the integrated lancing test strip 20 is pulled further, the cam arm 94 continues to rotate until the blade 112 disengages from the engagement notch 39 in the lancet 30. With the integrated lancing test strip 20 disengaged from the cam arm 94, the integrated strip 20 can then be completely removed from the meter 60 for disposal or further analysis, if so desired. For subsequent tests, new integrated lancing test strips 20 can then be loaded into the meter 60 in the manner as was describe above.

From the previous discussion, it should be appreciated that the integrated lancing test strip 20 as well as the meter 60 can be used to sample and analyze body fluid from various body parts like fingers and alternate sites, such as the forearm, for example. Moreover, the integrated lancing test strip 20 can be used to analyze numerous types of body fluids, such as interstitial fluid and blood, to name a few. It also should be recognized that the features of the integrated lancing test strip 20 can be modified for use in other types of meters besides the one illustrated in the drawings. Conversely, the above-described meter 60 can be used in conjunction with other types of sampling devices, besides the above-described integrated lancing test strip 20. Although the above-described integrated lancing test strip 20 and meter 60 were describe with reference to a single step test in which the lancing, any required expressing, sampling, and testing all occurred while the meter 60 remained in contact with the skin, it is contemplated that the integrated lancing test strip 20 and meter 60 can be used in a somewhat traditional two (or three) step process. That is, after lancing the skin, such as on a finger, the meter 60 can be removed from the skin such that the user can look at, and if needed, express fluid from the incision, such as for example by squeezing the finger. Once a sufficient amount of blood or other body fluid collects on the skin, the user can reposition the meter 60 such that the test strip 26 collects the fluid sample for analysis.

It is desirable to maintain the sterility of the lancet 30 as long as possible, but at the same time, it is desirable that the slit 132 be formed in the sterility sheet 24 so that the lancet 30 is able to be freely actuated without interference of the sterility sheet 24. Generally speaking, initial engagement of the cam arm 94 with lancet 30 can be done at several instances, including test strip loading; lancet priming; and firing cycle operations. In the previously described examples, the blade 112 on the cam arm 94 pierces or ruptures the sterility sheet 24 on the integrated lancing test strip 20 so that the blade 112 engages the engagement notch or opening 39 in the lancet 30 during loading of the integrated lancing test strip 20 (FIG. 15). However, once loaded, the lancet 30 may not be fired for some time such that the now compromised sterility sheet 24 may permit exposure of the lancet 30 to harmful contaminants. For example, a user might change his or her mind prior to use and unload the integrated lancing test strip 20. With the slit 132 formed in the sterility sheet 24 during loading, the lancet 30 can then be exposed to harmful contaminants. Premature exposure of lancet 30 can be especially harmful for integrated disposables that integrate together individual test strips and lancets into a single unit because the opportunity for cross-contamination between the lancet and test strip is increased. Consequently, it is desirable that the sterility sheet 24 be punctured during lancing so as to minimize the exposure time of the lancet 30 to the outside environment. In other words, only breaking the sterility sheet 24 close to and/or during the actual firing cycle preserves sterility and allows the integrated lancing test strip 20 to be inserted and removed from meter 60 without compromising the sterility, until actual lancing occurs. However, puncturing the sterility sheet 24 during lancing can create a whole host of other issues. For example, as noted before, the sterility sheet 24 can interfere with the movement of the cam arm 94 and the lancet 30 during lancing. Over time, the blade 112 on the cam arm 94 can dull due to repeated engagement with the engagement opening 39 in the lancet 30. The dullness of the blade 112 can lead to unsuccessful or incomplete puncturing of the sterility sheet 24, which in turn can lead to unsuccessful lancing.

Figure 19:
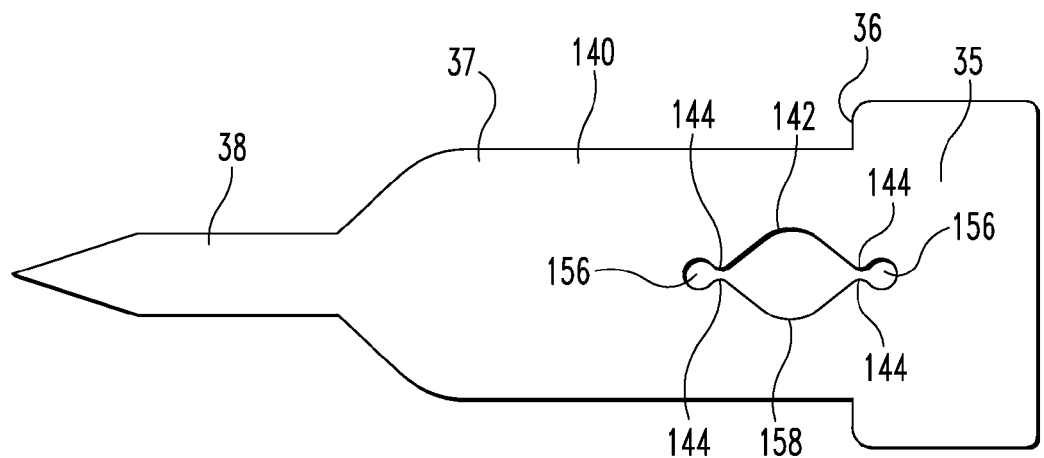
FIG. 19 is a top view of a lancet according to another embodiment.

A lancing system according to one embodiment that addresses the above-mentioned concerns will be initially described with reference to FIG. 19. As can be seen, FIG. 19 illustrates a lancet 140 that shares several features in common with the lancet 30 described above with reference to FIG. 7. For example, the lancet 140 has the body portion 35 with stop edges 36, the neck portion 37, and the tip 38. For the sake of brevity, these common features will not be again described in detail below, but reference is made to the previous discussion of these common features. In FIG. 19, the lancet 140 has an engagement opening (notch) or keyhole 142 that is configured to reduce dulling of the engagement blade of the firing mechanism. As shown, the engagement opening 142 has one or more engagement protrusions 144 that are configured in an opposing manner to engage the sides and not the cutting edges of the blade. Although the lancet 140 in the embodiment shown in the drawings has a single engagement opening 142, lancets 140 according to other embodiments can have more than one engagement opening 142. In the illustrated embodiment, the engagement opening 142 is shaped like a rounded diamond with circular cut outs in the top and bottom of the diamond shape, but it should be recognized from the discussion below that the engagement opening 142 can be shaped differently in other embodiments. For instance, the periphery of the engagement opening 142 is enclosed on all sides by the lancet 140, but in other embodiments, part of the periphery of the engagement opening 142 can be open, in other words, not enclosed by the lancet 140.

Figure 20:
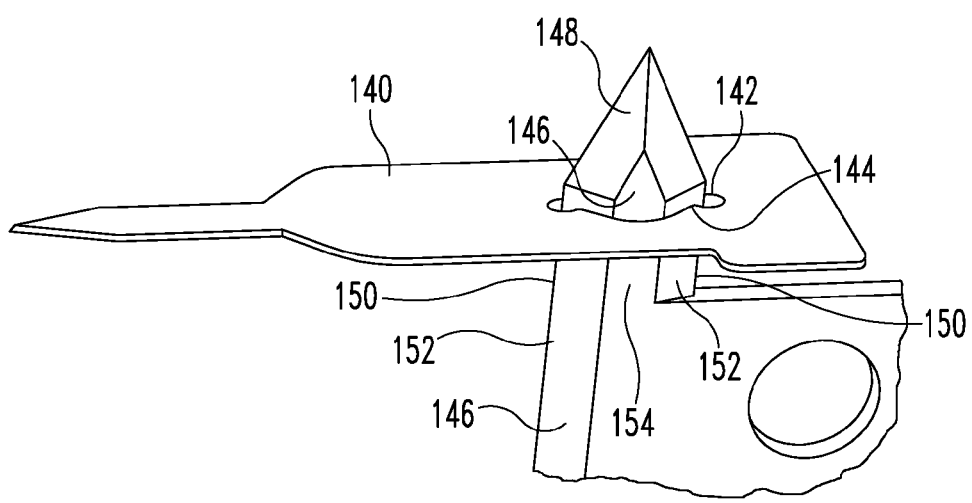
FIG. 20 is a perspective view of the FIG. 19 lancet engaged to an engagement blade of a firing mechanism.

FIG. 20 illustrates a blade 146 of a firing mechanism engaging the engagement opening 142 in the lancet 140. The blade 146 has a puncturing tip 148 that is shaped to pierce the sterility sheet 24. In the embodiment shown, the puncturing tip 148 generally has a pyramid shape, but the puncturing tip 148 can be shaped differently in other embodiments. The blade 146 in the depicted embodiment is a dual edge blade with opposing cutting edges 150 that are configured to cut a travel path or slit in the sterility sheet 24 during both firing and retraction of the lancet 140. It should be noted that, considering a slit is formed during firing, a second separate slit may not be always formed during retraction because the blade 146 may travel along the same path as the initial slit during firing. Nevertheless, the cutting edge 150 will still promote smooth retraction of the lancet 140. In the illustrated embodiment, the blade 146 has two cutting edges 150, but the blade 146 in other embodiments can have more or less cutting edges 150 than is shown. For example, the blade 146 in other embodiments can have a single cutting edge 150 that is positioned to slit the sterility sheet 24 as the lancet 140 is extended to lance the skin. Although the blade 146 is illustrated as a unitary structure, it is envisioned that components of the blade 146, such as the tip 148, cutting edges 150, and/or other functional components, can be separate. Moreover, it is envisioned that more than one blade 146 can be used at the same time.

Returning to the illustrated embodiment, the cutting edges 150 are defined by beveled blade surfaces 152, and the blade 146 has opposing sidewalls 154 disposed between the cutting edges 150. In the depicted embodiment, the cutting edges 150 extend towards one another at the blade tip 148 to form the point of the tip 148. It is envisioned that in other embodiments the opposing sidewalls 154 can be optional. Moreover, it is contemplated that the blade 146 can be shaped differently in other embodiments. For instance, the blade 146 in other embodiments can be a single-edged blade, a curved trailing-point blade, a clip-point blade, a sheepsfoot blade, and/or an Americanized tanto-style blade, to name just a few examples.

Figure 21:
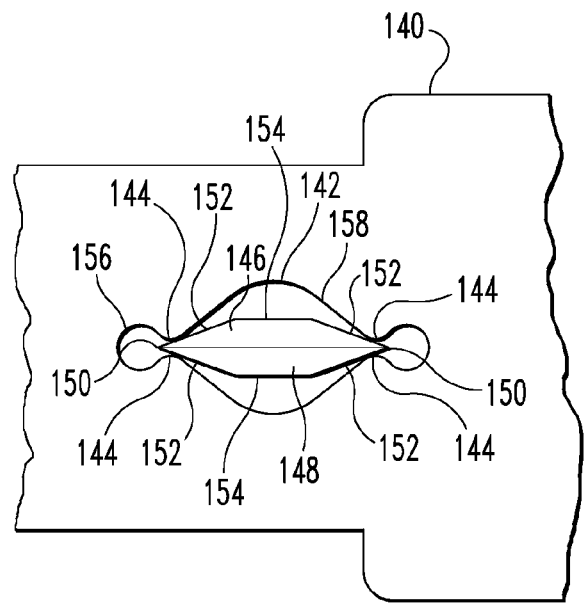
FIG. 21 is an enlarged top view of the FIG. 20 blade engaged in an engagement hole of the FIG. 19 lancet.

Turning to FIG. 21, the engagement protrusions 144 of the engagement opening 142 in the lancet 140 are configured to engage the angled blade surfaces 152 and not the cutting edges 150 of the blade 146. The engagement protrusions 144 provide point contacts at the blade surfaces 152, which in turn reduces the chances that the cutting edges 150 are dulled by contact with the lancet 140. The engagement protrusions 144 in the illustrated embodiment are rounded to prevent damage to the blade 146 and also help in centering the blade 146 during engagement with the lancet 140. At the cutting edges 150, the engagement opening 142 has one or more cut out portions 156 that prevent the cutting edges 150 of the blade 146 from contacting the lancet 140. With the cutting edges 150 not contacting the lancet 140, the chance of the cutting edges 150 of the blade 146 being dulled by rubbing against the lancet 140 during insertion and actuation is reduced. Between the cut out portions 156, the engagement opening 142 has a recessed section 158 that keeps the walls of the engagement opening 142 from contacting the blade 146. This configuration allows the blade 146 to contact the lancet 140 on the beveled surfaces 152 of the engagement blade 146, without touching the sharp cutting edges 150 of the engagement blade 146. As can be seen, the recessed section 158 is shaped like a rounded diamond and the cut out portions 156 are diamond shaped, but it should be appreciated that the engagement opening 142 can be shaped differently in other embodiments. For example, instead of having a circular shape, the cut out portions 156 in other embodiments can have an oval or square shape.

Figure 22:
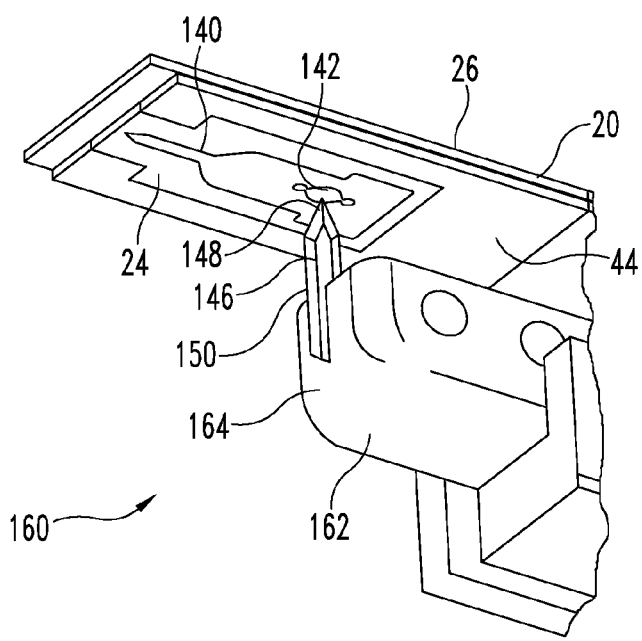
FIG. 22 is a perspective view of an integrated disposable that incorporates the FIG. 19 lancet when loaded in a meter prior to firing of the lancet.

As discussed above, it is desirable to maintain the integrity of the lancet packet 44 as long as possible so as to minimize the chance for contamination of the lancet 140. A technique according to one embodiment for actuating the lancet 140 in order to achieve this result will now be described with reference to FIGS. 22, 23, and 24. Referring to FIG. 22, the lancet 140 is incorporated into the integrated lancing test strip 20 of the type described above, which is commonly referred to as a lancet integrated test strip or "LIT" for short. As noted before, the LIT 20 includes the sterility sheet 24 that seals the lancet 140 inside the lancet packet 44, and the lancet packet 44 is attached to the test strip 26 to form the LIT 20. Prior to lancing, the LIT 20 is loaded into a meter 160 that includes a firing mechanism 162. Unlike the previous embodiments, the sterility sheet 24 remains intact such that the lancet packet 44 remains sealed during loading of the LIT 20. The firing mechanism 162 in the meter 160 includes a firing (cam) arm 164 from which the engagement blade 146 extends. Once the LIT 20 is loaded, the engagement opening 142 of the lancet 140 is positioned proximal the blade 146 of the firing mechanism 162. During priming of the firing mechanism 162, the blade 146 of the firing mechanism 162 remains in a retracted state relative to the engagement opening 142 in one embodiment such that the sterility sheet 24 remains unpierced prior to lancing. However, as will be explained below, the blade 146 in another embodiment pierces the sterility sheet 24 during priming.

Figure 23:
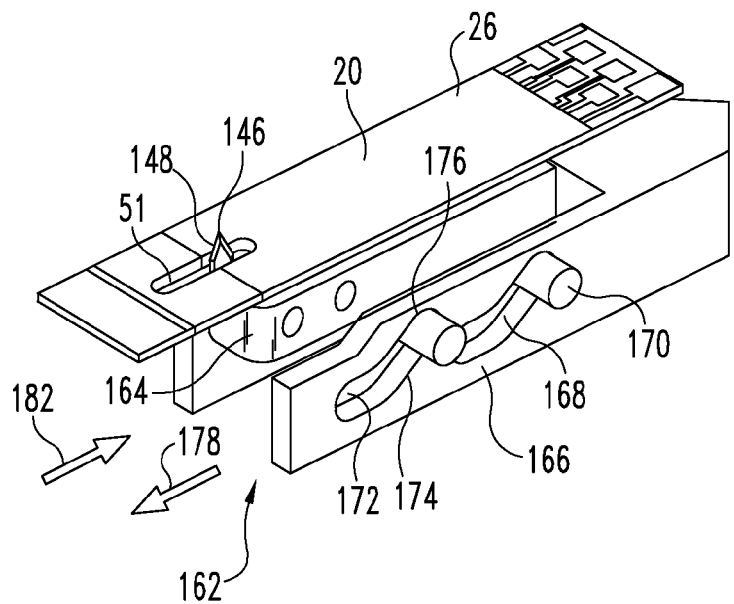
FIG. 23 is a perspective view of the FIG. 22 integrated disposable engaged with a firing mechanism of the FIG. 22 meter during firing of the FIG. 19 lancet.

Looking at FIG. 23, the firing mechanism 162 includes a plunger or actuator arm 166 that is used to actuate the firing arm 164. The plunger 166 can be actuated via a number of manners, such as via mechanical, pneumatic, and/or electrical actuation, to name a few. In one example, the plunger 166 is attached to a spring-type firing mechanism, and in another example, an electric motor is used to actuate the plunger 166. The plunger 166 has one or more cam slots 168 in which one or more cam pins 170 of the firing arm 164 are slidably received. In the illustrated embodiment, the firing arm 164 has a pair of cam pins 170 on opposing sides of the firing arm 164, but it should be understood that the more or less cam slots 168 and cam pins 170 can be used. The cam slots 170 each include a retraction section 172, an angled actuation section 174, and an engagement section 176. When the cam pins 170 are in the retraction section 172, the blade 146 is disengaged from the lancet 140, as is depicted in FIG. 22. As the plunger 166 is fired in a firing direction 178, the cam pins 170 travel in the actuation section 174 which in turn causes the tip 148 of the blade 146 to extend towards the engagement opening 142 in the lancet 140 and pierce the sterility sheet 24. Once the cam pins 170 reach the engagement section 176 of the cam slots 168, the blade 146 is fully engaged with the engagement slot 142 in the lancet 140. As can be seen, the tip 148 of the blade 146 extends through the relief opening 51 in the test strip 20. It should be recognized that other types of firing mechanisms can be used in other embodiments to position and actuate the blade 146.

Figure 24:
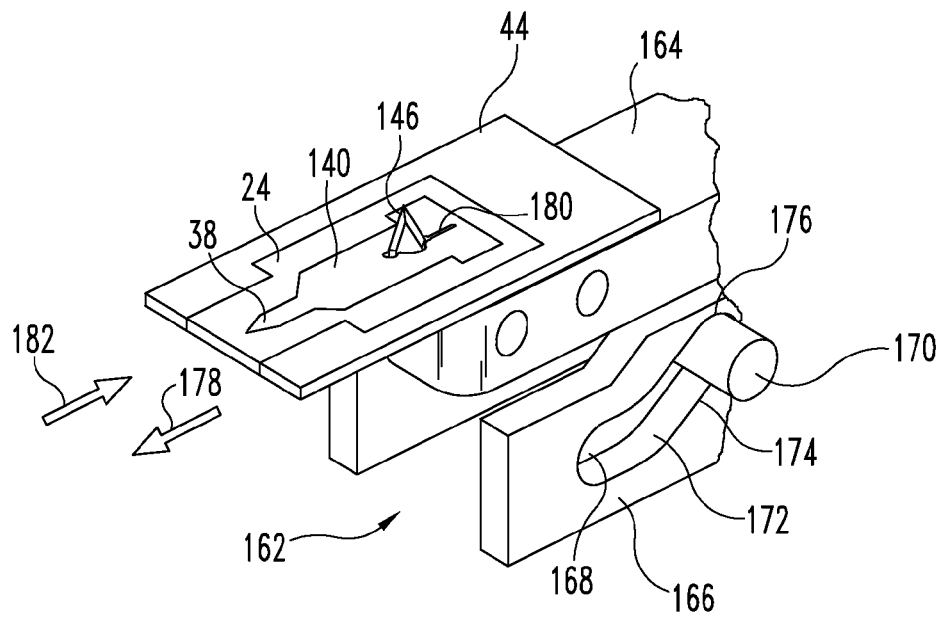
FIG. 24 is an enlarged view of FIG. 23 with the test strip of the integrated disposable removed.

In FIG. 24, the test strip 20 has been removed solely to show how the blade 146 fully engages with the engagement slot 142 in the lancet 140. Of course, during actual use, the test strip 20 remains attached to the lancet packet 44, as is shown in FIG. 23. In the illustrated embodiment, the blade 146 pierces through both sheets 24 (sides) of the lancet packet 44 during engagement, but in other embodiments, the blade 146 may only puncture one side of the lancet packet 44. While the plunger 166 continues to move in the firing direction 178, the lancet 140 is fired towards the skin, and the leading cutting edge 150 (FIG. 22) of the blade 146 cuts one or more slits 180 in the sterility sheet 24 that create a travel opening or path in which the blade 146 can actuate the lancet 140 nearly without interference from the sterility sheet 24. As mentioned before, the blade 146 in the illustrated embodiment punctures both sides of the lancet packet 44 such that two slits 180 are formed on opposite sides of the lancet packet 44. However, more or less slits 180 can be cut in other embodiments. For example, when the blade 146 punctures only one side of the lancet packet 44, then only one slit 180 is formed, and when the lancet packet 44 has multiple layers of the sterility sheet 24 (or other sheets), the blade 146 will cut multiple slits 180. While the lancet 140 continues to advance in the firing direction 178, the cutting edge 150 continues to cut the slit 180 in the sterility sheet 24. As noted before, forming a slit or some other type of travel opening/path in the sterility sheet 24 helps to ensure that the lancet 140 travels smoothly during both the firing and retraction strokes. If this did not occur, the lancet 140 in some instances might bind with the sterility sheet 24, which can undesirably lead to insufficient lancing and/or retraction of the lancet 140. As discussed above, the shape of the engagement opening 142 in the lancet 140 ensures that the cutting edges 150 of the blade 146 remain sharp so that the blade 146 is able to consistently puncture and cut slits 180 in the lancet packet 44.

Eventually, as the lancet 140 advances, the tip 38 of the lancet 140 pierces or ruptures the sterility sheet 24, and the tip 38 of the lancet 140 extends from the lancet packet 44 in order to lance the skin. After the lancet 140 pierces the skin to the desired depth, the plunger 166 moves in a retraction direction 182, thereby retracting the lancet 140 from the incision and disengaging the blade 146 from the engagement opening 142 in the lancet. When the blade 146 has dual cutting edges 150, like is shown in the drawings, the cutting edge 150 facing the retraction direction 182 helps reduce the chance of the sterility sheet 24 interfering with the movement of the lancet 140 in the retraction direction 182. Afterwards, the now used LIT 20 can be removed from the meter 160, and a new LIT 20 can be loaded and fired in the same manner as described above. As should be recognized, this technique in which the lancet packet 44 is pierced during firing of the lancet 140 helps to ensure that the sterility of the lancet 140 is maintained as long as possible.

As alluded to above, in another variation of this technique, the blade 146 initially ruptures the sterility sheet 24 to engage the engagement slot 142 of the lancet 140 during priming of the firing mechanism 162. For example, the rupturing of the sterility sheet 24 can occur as a result of the operator cocking the firing mechanism 162. It was discovered that initially rupturing the sterility sheet 24 during the firing cycle on occasion robbed the firing mechanism 162 of the energy required to consistently lance the skin in a successful manner. Although there might be a rare incident when the operator primes the firing mechanism 162 but does not fire the lancet 140 for some time thereafter, it was found that such incidents are rare and the exposure times are relatively short such that risk of lancet contamination was insignificant, especially when compared against the harmful side effects of improper lancing. In one variation, the blade 146 punctures the sterility sheet 24 during priming, and the blade 146 cuts the slit 180 in the sterility sheet 24 during the firing cycle in the manner as depicted in FIG. 24. To further reduce the amount of energy wasted during firing, the blade 146 in a further variation cuts the slit 180 in the sterility sheet 24 and engages the engagement slot 142 in the lancet 140 during priming in a manner similar to the slitting illustrated in FIG. 15. In still yet another variation, the blade 146 slits the sterility sheet 24 during priming and engages the engagement slot 142 during the firing cycle. With all three of these variations, the sterility sheet 24 is ruptured to some extent before the firing cycle so as to conserve energy during the firing cycle of the lancet 140.

Figure 25:
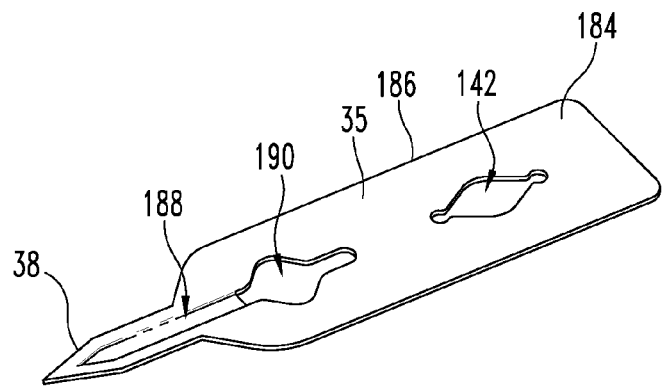
FIG. 25 is a perspective view of a lancet for a microsampler according to another embodiment.
Figure 26:
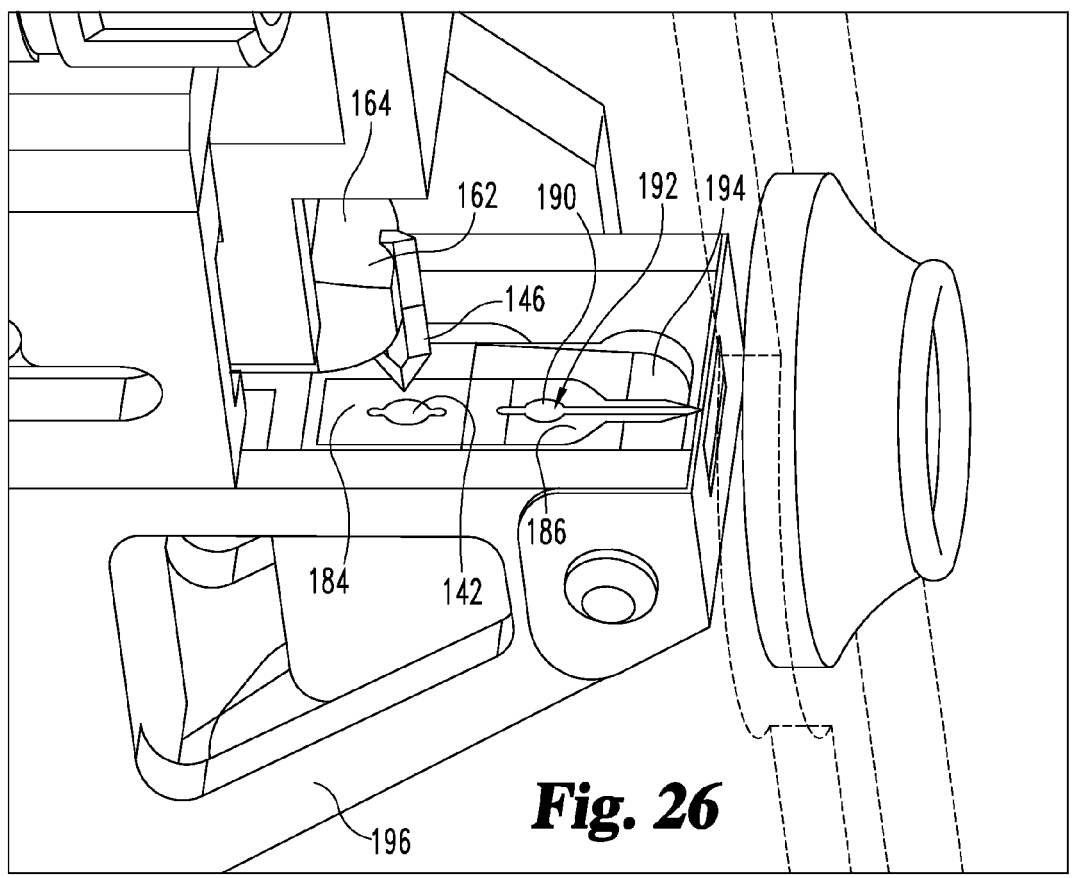
FIG. 26 is a perspective view of the FIG. 25 microsampler loaded in a meter.

It should be appreciated that the engagement opening 142 shown in FIG. 19 and the above-discussed techniques can be incorporated into other types of fluid sampling systems. For instance, the engagement opening 142 of FIG. 19 can be incorporated into a microsampler 184 of the type illustrated in FIGS. 25 and 26. The microsampler 184 includes a lancet 186 that has body portion 35 and tip 38. The lancet 186 has a capillary groove 188 that is used to transport a body fluid sample from an incision to a sample transfer opening or pooling area 190 in the lancet 30. From the pooling area 190, the fluid sample is transferred to a testing area or reagent pad 192 where the sample is analyzed. It should be recognized that the pooling area 190 can be eliminated or shaped differently in other embodiments. In the embodiment depicted in FIG. 26, the microsampler 184 is attached to a transport tape 194 that has the reagent pad 192, and the tape 194 is stored in a cassette 196 that stores multiple microsamplers 184. The microsampler 184 is fired by the firing mechanism 162 that includes the firing arm 164 and blade 146 of the type described above with reference to FIGS. 23 and 24. Additional details about the microsampler 184 are provided in U.S. patent application Ser. No. 11/549,302, filed Oct. 13, 2006 entitled "Tape Transport Lance Sampler", which is hereby incorporated by reference.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected. All publications, patents, and patent applications cited in this specification are herein incorporated by reference as if each individual publication, patent, or patent application was specifically and individually indicated to be incorporated by reference as set forth in its entirety herein. Any document incorporated by reference is incorporated to the extent that the teachings of the document are consistent with the teachings of the present application. The incorporation by reference of these documents in no way should limit the scope of protection provided by the claims and/or narrow the meaning of terms used in the claims.

What is claimed is:
1. An apparatus, comprising:
   a lancet defining an engagement opening, wherein the engagement opening is in the lancet;
   a firing mechanism to fire the lancet, the firing mechanism including an engagement blade that is configured to engage with the engagement opening of the lancet, the engagement blade having one or more cutting edges;
   the engagement opening having one or more cut out portions at the one or more cutting edges when the blade engages the engagement opening to minimize dulling of the one or more cutting edges of the engagement blade; and
   wherein the lancet is sealed inside a sterility sheet to form a lancet packet.

2. The apparatus of claim 1, wherein the engagement opening of the lancet has one or more engagement protrusions configured to contact the blade at a location other than at the one or more cutting edges.

3. The apparatus of claim 2, wherein the one or more engagement protrusions are rounded to prevent damage to the blade.

4. The apparatus of claim 1, wherein the one or more cut out portions have a circular shape.

5. The apparatus of claim 4, wherein the engagement opening has a recessed section that is diamond shaped.

6. The apparatus of claim 5, wherein:
   the engagement blade has two of the cutting edges; and
   the engagement opening has two of the circular shaped cut out portions that are disposed on opposite ends of the diamond shaped recessed section.

7. The apparatus of claim 1, wherein the one or more cutting edges of the engagement blade are configured to cut one or more slits in the sterility sheet of the lancet packet to promote smooth actuation of the lancet.

8. The apparatus of claim 1, wherein the engagement blade of the firing mechanism has a tip configured to puncture the sterility sheet during engagement with the engagement opening of the lancet.

9. The apparatus of claim 8, wherein the firing mechanism is configured to puncture the sterility sheet with the tip of the blade during firing of the lancet.

10. The apparatus of claim 9, wherein the firing mechanism includes:
    a firing arm secured to the engagement blade, the firing arm including one or more cam pins;
    a plunger defining one or more cam slots in which the one or more cam pins are slidably received; and
    wherein the one or more cam slots are shaped to move the engagement blade to puncture the sterility sheet with the tip of the blade when the plunger is fired.

11. The apparatus of claim 1, further comprising a test strip attached to the lancet packet.

12. The apparatus of claim 1, wherein the lancet defines a capillary groove configured to draw body fluid via capillary action.

13. An apparatus, comprising:
    a lancet defining an engagement opening where the lancet is coupled to a firing mechanism, wherein the engagement opening is in the lancet; and
    wherein the engagement opening is shaped like a rounded diamond with circular cut outs at opposite ends of the diamond.

14. The apparatus of claim 13, further comprising a test strip coupled to the lancet to analyze a body fluid sample.

15. The apparatus of claim 14, further comprising a lancet packet in which the lancet is sealed inside in a sterile manner.

16. The apparatus of claim 13, wherein the lancet defines a capillary groove configured to draw a body fluid sample via capillary action.

17. An apparatus, comprising:
    a firing mechanism configured to fire a lancet that is sealed inside a lancet packet for cutting an incision in skin; and the firing mechanism including
an engagement blade configured to engage the lancet,
the engagement blade having a cutting edge positioned to cut a slit in the lancet packet for facilitating smooth actuation of the lancet;
wherein the firing mechanism is configured to retract the lancet; and
wherein the engagement blade includes a second cutting edge positioned to form a second slit in the lancet packet as the engagement blade retracts the lancet.

18. The apparatus of claim 17, further comprising:
the lancet;
the lancet packet;
a test strip attached to the lancet packet; and
the firing mechanism being configured to pierce the lancet packet with the blade and cut the slit during firing of the lancet to minimize cross-contamination between the lancet and the test strip.

19. The apparatus of claim 17, wherein the firing mechanism is configured to cut the slit during priming to conserve energy for firing of the lancet.

20. The apparatus of claim 17, wherein the firing mechanism is configured to cut the slit during loading of the lancet.

21. The apparatus of claim 17, further comprising:
the lancet;
the lancet packet; and
the lancet defining an engagement opening in which the engagement blade is received, the engagement opening being shaped like a rounded diamond with circular cut outs at opposite ends of the diamond to reduce dulling of the cutting edge of the blade.

22. An apparatus, comprising:
a lancet sealed inside a lancet packet to maintain sterility of the lancet;
a test strip attached to the lancet packet;
a firing mechanism including an engagement blade configured to engage with the lancet, the firing mechanism being configured to pierce the lancet packet with the blade;
wherein the lancet has an engagement opening in which the engagement blade is received; and
wherein the test strip has a relief slot configured to receive at least a portion of the engagement blade when engaged with the engagement opening of the lancet.

23. The apparatus of claim 22, wherein:
the engagement opening is shaped like a rounded diamond with circular cut outs at opposite ends of the diamond to reduce dulling of the blade.

24. The apparatus of claim 22, wherein the firing mechanism is configured to pierce the lancet packet during firing of the lancet to minimize cross-contamination between the lancet and the test strip.

25. The apparatus of claim 22, wherein the firing mechanism is configured to pierce the lancet packet during priming to cut a travel path in the lancet packet for the blade.

26. A method, comprising:
engaging a blade of a firing mechanism with a lancet that is enclosed inside a packet, wherein the blade includes a first cutting edge and a second cutting edge; firing the lancet with the firing mechanism by advancing the lancet with the blade to form an incision in skin;
forming a slit in the packet with the first cutting edge of the blade, wherein said forming the slit in the packet occurs during said firing; and
forming a second slit in the packet with the second cutting edge of the blade by retracting the lancet with the blade after forming the incision.

27. The method of claim 26, further comprising:
reducing dulling of the blade by providing an engagement opening that is shaped like a rounded diamond with circular cut outs at opposite ends of the diamond; and
inserting the blade into the engagement opening.

28. The method of claim 26, further comprising:
priming the firing mechanism; and
forming the slit in the packet during said priming.

29. The method of claim 26, further comprising:
loading the packet into the firing mechanism; and
forming the slit in the packet during said loading.

30. The method of claim 26, wherein said engaging the blade occurs before forming the slit in the packet.

31. The method of claim 26, wherein said engaging the blade occurs after forming the slit in the packet.

32. The method of claim 26, further comprising:
wherein the packet is attached to a test strip;
forming an incision in the skin with the lancet; and
analyzing body fluid from the incision in the skin with the test strip.

33. A method, comprising:
loading a lancet integrated test strip into a meter that includes a firing mechanism, wherein the lancet integrated test strip includes a lancet sealed inside a lancet packet and a test strip attached to the lancet packet, wherein the firing mechanism includes a blade that has a cutting edge;
reducing cross-contamination risk between the lancet and the test strip by piercing the lancet packet after said loading the lancet integrated test strip;
engaging the blade of the firing mechanism into an engagement opening that has a cut out portion positioned proximal the cutting edge of the blade to reduce dulling of the cutting edge;
firing the lancet with the firing mechanism to cut an incision in skin;
slitting the lancet packet with the cutting edge of the blade during said firing; and
analyzing a body fluid sample from the incision with the test strip.

34. The method of claim 33, further comprising:
priming the firing mechanism;
wherein the firing mechanism includes a blade; and
wherein said slitting the lancet packet occurs during said priming.

35. A method, comprising:
inserting an engagement blade of a firing mechanism inside an engagement opening in a lancet, wherein the lancet is sandwiched to a test strip that has a relief slot;
wherein said inserting the engagement blade includes receiving at least a portion of the engagement blade in the relief slot of the test strip;
firing the lancet by actuating the engagement blade of the firing mechanism; and
wherein the portion of the engagement blade received in the relief slot travels inside the relief slot during said firing of the lancet.

36. The method of claim 35, further comprising:
wherein the lancet is enclosed inside a lancet packet that maintains lancet sterility; and
slitting the lancet packet with the engagement blade.

37. The method of claim 36, further comprising:
loading the lancet packet into the firing mechanism; and
wherein said slitting the lancet packet occurs during said loading.

38. The method of claim 36, further comprising:
wherein said slitting the lancet packet occurs during said firing.

39. The method of claim 36, further comprising:
priming the firing mechanism; and
wherein said slitting the lancet packet occurs during said priming.

40. The method of claim 36, further comprising:
wherein the engagement blade includes first and second cutting edges; and
forming a second slit in the lancet packet with the second cutting edge of the engagement blade by retracting the lancet after said firing.

41. The method of claim 40, further comprising:
wherein the engagement opening is shaped like a rounded diamond with circular cut outs at opposite ends of the diamond; and
reducing dulling of the engagement blade by aligning the first and second cutting edges in the circular cut outs of the engagement opening during said inserting the engagement blade.

42. The apparatus of claim 1, wherein the engagement blade of the firing mechanism is configured to pierce the sterility sheet of the lancet packet.

* * * * *

UNITED STATES PATENT AND TRADEMARK OFFICE
CERTIFICATE OF CORRECTION

PATENT NO.         : 7,935,063 B2                                    Page 1 of 1
APPLICATION NO.    : 11/551414
DATED              : May 3, 2011
INVENTOR(S)        : Steven N. Roe It is certified that error appears in the above-identified patent and that said Letters Patent is hereby corrected as shown below:

Patent front page, (73) Assignee, replace "Indianapolis, MN (US)" with --Indianapolis, IN (US)--

Signed and Sealed this
Fourteenth Day of June, 2011

David J. Kappos
*Director of the United States Patent and Trademark Office*